United States Patent
Donhowe et al.

(10) Patent No.: US 11,202,680 B2
(45) Date of Patent: Dec. 21, 2021

(54) SYSTEMS AND METHODS OF REGISTRATION FOR IMAGE-GUIDED SURGERY

(71) Applicant: INTUITIVE SURGICAL OPERATIONS, INC., Sunnyvale, CA (US)

(72) Inventors: Caitlin Q. Donhowe, Mountain View, CA (US); Tao Zhao, Sunnyvale, CA (US); Vincent Duindam, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 332 days.

(21) Appl. No.: 15/752,166

(22) PCT Filed: Aug. 11, 2016

(86) PCT No.: PCT/US2016/046636
§ 371 (c)(1),
(2) Date: Feb. 12, 2018

(87) PCT Pub. No.: WO2017/030915
PCT Pub. Date: Feb. 23, 2017

(65) Prior Publication Data
US 2018/0235709 A1    Aug. 23, 2018

Related U.S. Application Data

(60) Provisional application No. 62/205,433, filed on Aug. 14, 2015.

(51) Int. Cl.
*A61B 34/20* (2016.01)
*A61B 34/30* (2016.01)
(Continued)

(52) U.S. Cl.
CPC ............ *A61B 34/20* (2016.02); *A61B 1/0016* (2013.01); *A61B 5/0066* (2013.01); *A61B 5/015* (2013.01);
(Continued)

(58) Field of Classification Search
CPC ......... A61B 34/20; A61B 34/30; A61B 34/35; A61B 90/37; A61B 1/0016; A61B 5/0066;
(Continued)

(56) References Cited

U.S. PATENT DOCUMENTS 6,075,905 A * 6/2000 Herman .................. G06K 9/32
348/588
6,380,732 B1    4/2002 Gilboa
(Continued)

FOREIGN PATENT DOCUMENTS

CN    101051387 A    10/2007
CN    102428496 A    4/2012
(Continued)

OTHER PUBLICATIONS

International Search Report and Written Opinion for Application No. PCT/US16/46636, dated Nov. 18, 2016, 15 pages.
(Continued)

*Primary Examiner* — Amelie R Davis
*Assistant Examiner* — John Denny Li
(74) *Attorney, Agent, or Firm* — Haynes and Boone, LLP

(57) ABSTRACT

A method comprises segmenting first modality image data representing a model of one or more passageways within a patient; generating a first set of points based on the segmented image data; registering the first set of points to a second set of points obtained by a second modality by: determining a set of matches between the first and second sets of points, and discarding a first subset of the set of
(Continued)

matches based on a heuristic to generate a modified set of matches by ignoring an associated set of matches between the first and second sets of points when computing a corrective motion for the second set of points—an ignored match is included in a second subset of the set of matches when computing a second corrective motion for the second set of points; and displaying a visual representation of the passageways based on the modified set of matches.

20 Claims, 17 Drawing Sheets

(51) Int. Cl.
| | |
|---|---|
| *A61B 1/00* | (2006.01) |
| *G06T 7/12* | (2017.01) |
| *G06T 7/33* | (2017.01) |
| *A61B 34/35* | (2016.01) |
| *A61B 90/00* | (2016.01) |
| *A61B 5/00* | (2006.01) |
| *A61B 5/01* | (2006.01) |
| *A61B 5/0536* | (2021.01) |
| *A61B 5/055* | (2006.01) |
| *A61B 5/06* | (2006.01) |
| *A61B 6/03* | (2006.01) |
| *A61B 8/08* | (2006.01) |
| *A61B 34/10* | (2016.01) |
| *A61B 17/00* | (2006.01) |

(52) U.S. Cl.
CPC ............ *A61B 5/055* (2013.01); *A61B 5/0536* (2013.01); *A61B 5/062* (2013.01); *A61B 5/066* (2013.01); *A61B 6/032* (2013.01); *A61B 8/0841* (2013.01); *A61B 34/30* (2016.02); *A61B 34/35* (2016.02); *A61B 90/37* (2016.02); *G06T 7/12* (2017.01); *G06T 7/33* (2017.01); *G06T 7/344* (2017.01); *A61B 2017/00699* (2013.01); *A61B 2017/00809* (2013.01); *A61B 2034/105* (2016.02); *A61B 2034/107* (2016.02); *A61B 2034/2051* (2016.02); *A61B 2034/2061* (2016.02); *A61B 2034/2065* (2016.02); *A61B 2034/301* (2016.02); *A61B 2090/0811* (2016.02); *A61B 2090/3937* (2016.02); *G06T 2200/24* (2013.01); *G06T 2207/10068* (2013.01); *G06T 2207/10081* (2013.01); *G06T 2207/10088* (2013.01); *G06T 2207/10116* (2013.01); *G06T 2207/30061* (2013.01); *G06T 2207/30172* (2013.01)

(58) Field of Classification Search
CPC ....... A61B 5/015; A61B 5/0536; A61B 5/055; A61B 5/062; A61B 5/066; A61B 6/032; A61B 8/0841; A61B 2034/105; 2034/107; A61B 2034/2051; A61B 2034/2061; A61B 2034/2065; A61B 2034/301; A61B 2090/0811; A61B 2090/3937; A61B 2017/00699; A61B 2017/00809; G06T 7/12; G06T 7/344; G06T 7/33; G06T 2200/24; G06T 2207/10068; G06T 2207/10081; G06T 2207/10088; G06T 2207/10116; G06T 2207/30061; G06T 2207/30172
See application file for complete search history.

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,772,541 | B2 | 8/2010 | Froggatt et al. |
| 7,981,038 | B2 | 7/2011 | Kanade et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 10,706,543 | B2 | 7/2020 | Donhowe et al. |
| 2003/0083850 | A1* | 5/2003 | Schmidt .................. G06T 7/001 702/189 |
| 2005/0182295 | A1 | 8/2005 | Soper et al. |
| 2006/0013523 | A1 | 1/2006 | Childlers et al. |
| 2006/0184016 | A1 | 8/2006 | Glossop et al. |
| 2007/0167801 | A1* | 7/2007 | Webler .................... G06T 19/00 600/459 |
| 2008/0118135 | A1 | 5/2008 | Averbuch et al. |
| 2009/0227861 | A1 | 9/2009 | Ganatra et al. |
| 2010/0034440 | A1* | 2/2010 | Zhan ........................ G06T 7/33 382/128 |
| 2010/0067755 | A1 | 3/2010 | Chan et al. |
| 2012/0069167 | A1 | 3/2012 | Liu et al. |
| 2012/0289777 | A1 | 11/2012 | Chopra et al. |
| 2013/0096572 | A1 | 4/2013 | Donhowe et al. |
| 2013/0231556 | A1 | 9/2013 | Holsing et al. |
| 2013/0274596 | A1 | 10/2013 | Azizian et al. |
| 2013/0303892 | A1 | 11/2013 | Zhao et al. |
| 2014/0122112 | A1 | 5/2014 | Bzdusek et al. |
| 2015/0157267 | A1 | 6/2015 | Shushan et al. |
| 2015/0164596 | A1 | 6/2015 | Romo et al. |
| 2017/0213354 | A1* | 7/2017 | Glinec ................... G06T 15/10 |
| 2017/0265953 | A1 | 9/2017 | Fenech et al. |
| 2018/0221634 | A1 | 8/2018 | Hazan et al. |
| 2019/0220976 | A1* | 7/2019 | Holsing ................ G06T 7/0012 |
| 2020/0364865 | A1 | 11/2020 | Donhowe |

FOREIGN PATENT DOCUMENTS

| | | |
|---|---|---|
| EP | 2881037 A1 | 6/2015 |
| WO | WO-2010133982 A2 | 11/2010 |
| WO | WO-2011128797 A1 | 10/2011 |
| WO | WO-2016191298 A1 | 12/2016 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2016/46633, dated Mar. 1, 2018, 5 pages.
International Preliminary Report on Patentability for Application No. PCT/US2016/46636, dated Mar. 1, 2018, 11 pages.
Extended European Search Report for Application No. EP16837556. 6, dated Apr. 2, 2019, 12 pages.
Semino A., et al., "Image Registration by a Region Based Approach and by Correction of Elastic Deformations," Signal Processing Theories and Applications, Proceedings of European Signal Processing Conference, Aug. 1992, vol. 3, pp. 1441-1444.
Zhong H., et al., "Virtual Touch: An Efficient Registration Method for Catheter Navigation in Left Atrium," Medical Image Computing and Computer-assisted Intervention, Jan. 2006, vol. 9 (Pt 1), pp. 437-444.
Office Action dated Sep. 24, 2019 for Chinese Application No. CN20168047529 filed Aug. 11, 2016, 15 pages.
Extended European Search Report for Application No. EP20207368.0 dated Feb. 15, 2021, 10 pages.
Pomerleau, F et.al., "A Review of Point Cloud Registration Algorithms for Mobile Robotics," Foundations and Trends in Robotics, Jul. 2015, vol. 4 (1), pp. 1-104.

* cited by examiner

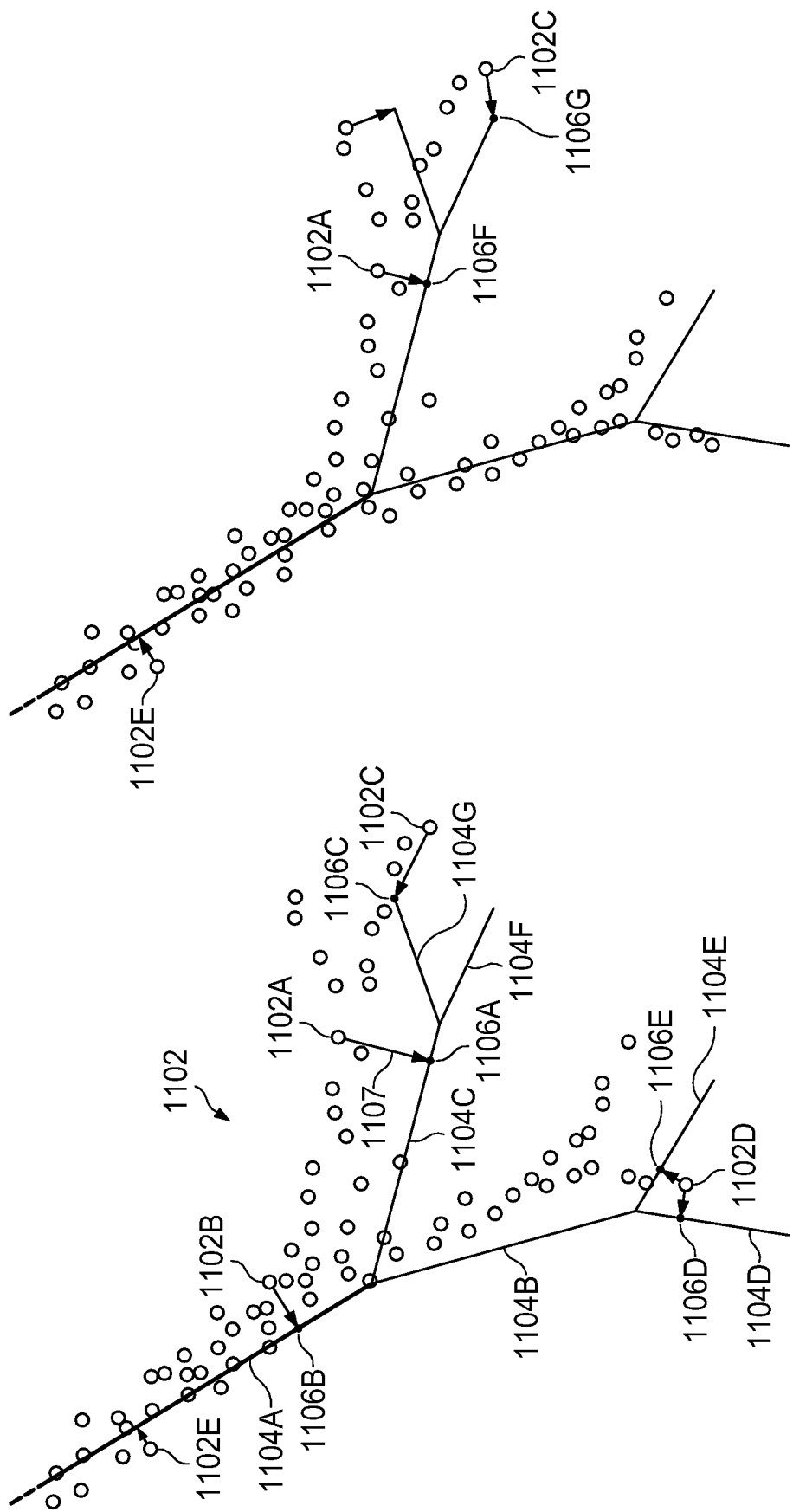

| POINT ID | COORDINATES (X,Y,Z) | TIMESTAMP | SENSOR ID | PHASE MARKER | WEIGHT |
|---|---|---|---|---|---|
| 00152 | 45.017, 26.029, 33.793 | 00:00:59 | 001 | 1 | 0.05 |
| 00153 | 45.028, 26.1, 35.201 | 00:01:02 | 003 | 0 | 0.06 |
| 05678 | 22.650, 39.825, 2.091 | 01:29:37 | 124 | 1 | 1 |
| 01297 | 37.629, 30.5, 20.2 | 00:45:53 | 032 | 0 | 0.3 |
| 12028 | 38.9, 3.5, 10.1 | 00:59:37 | NA | 0 | 0.6 |
| 07078 | 29.6, 28.2, 20.0 | 00:14:32 | 237 | 1 | 0.1 |

SYSTEMS AND METHODS OF REGISTRATION FOR IMAGE-GUIDED SURGERY

RELATED APPLICATIONS

This patent application is the U.S. national phase of International Application No. PCT/US2016/046636, filed Aug. 11, 2016, which designated the U.S. and claims priority to and the benefit of the filing date of U.S. Provisional Patent Application 62/205,433, entitled "SYSTEMS AND METHODS OF REGISTRATION FOR IMAGE-GUIDED SURGERY," filed Aug. 14, 2015, which is are incorporated by reference herein in its their entireties.

FIELD

The present disclosure is directed to systems and methods for conducting an image-guided procedure, and more particularly to systems and methods for displaying pathology data for tissue sampled during an image-guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of patient pads during pre-operative and operative imaging and may disturb the clinical environment or workflow. Systems and methods for performing image-guided surgery with minimal clinical disturbances are needed.

SUMMARY

The embodiments of the invention are best summarized by the claims that follow the description.

However, an exemplary method may include segmenting a set of first modality image data representing a model of one or more passageways within a patient and generating a first set of points based on the segmented set of first modality image data representing the model of the one or more passageways. The method may further include determining a set of matches between a second set of points and the first set of points, wherein the second set of points is obtained by a second modality and discarding a subset of the set of matches based on a first heuristic to generate a modified set of matches.

Another exemplary method may include receiving a set of model points of a model of one or more passageways of a patient and receiving a set of measured points collected from within the patient passageways, each point comprising coordinates within a surgical environment occupied by the patient. Weights may be assigned to one or more of the measured points. The method may further include matching each measured point to a model point to generate a set of matches, a value of each of the matches depending on the assigned weight of the measured point in the match, and moving the set of measured points relative to the set of model points based on the set of matches.

Another exemplary method may include receiving a set of measured points collected from within the patient passageways, each point comprising coordinates within a surgical environment occupied by the patient, and identifying features of the patient passageways based on the set of measured points. The method may further include steps or operations of identifying corresponding features, to the identified features, in a model of the patient passageways obtained prior to receiving the set of measured points, and of performing an initial registration of the set of measured points to a set of modeled points obtained from the model.

An addition exemplary method may include accessing a set of model points of a model of one or more passageways of a patient, detecting a point collection condition in data obtained from a catheter, initiating collection of a set of measured points, and performing a point set registration algorithm using the set of model points and the set of measured points.

Another additional exemplary method may include receiving a set of model points of a model of one or more passageways of a patient and receiving a first set of measured points collected from within the patient passageways, each point including coordinates within a surgical environment occupied by the patient. The method may further include operations of generating a first registration between the set of measured points and the set of model points, generating a second registration between a second set of measured points and the set of model points, and then determining whether to implement the second registration in place of the first registration.

Another exemplary method may include receiving a set of model points of a model of one or more passageways of a patient and determining a state of a catheter positioned within the one or more passageways of the patient. When the state of the catheter satisfies a condition, the method may further include collecting a set of measured points from within the patient passageways, each point comprising coordinates within a surgical environment occupied by the patient, and then generating a registration between the set of measured points and the set of model points.

Yet another exemplary method may include receiving a set of model points of a model of one or more passageways of a patient and receiving a first set of measured points collected from within the patient passageways, each point comprising coordinates within a surgical environment occupied by the patient. The method may further include generating a first registration between the set of measured points and the set of model points, detecting a motion of the patient, and generating a second registration between a second set of measured points and the set of model points.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 5A:
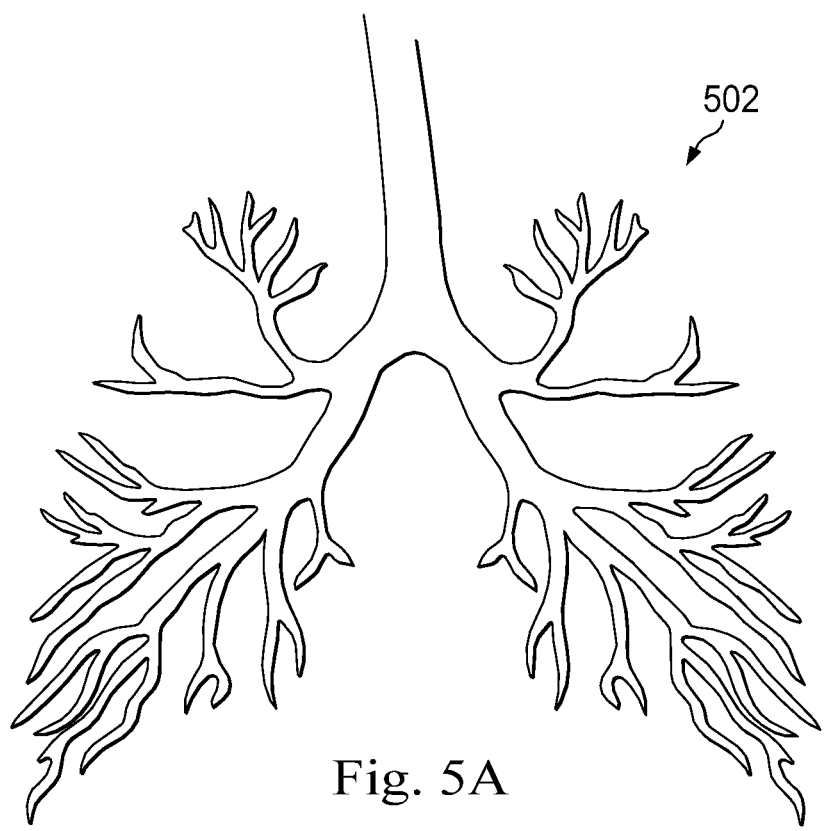
Figure 5B:
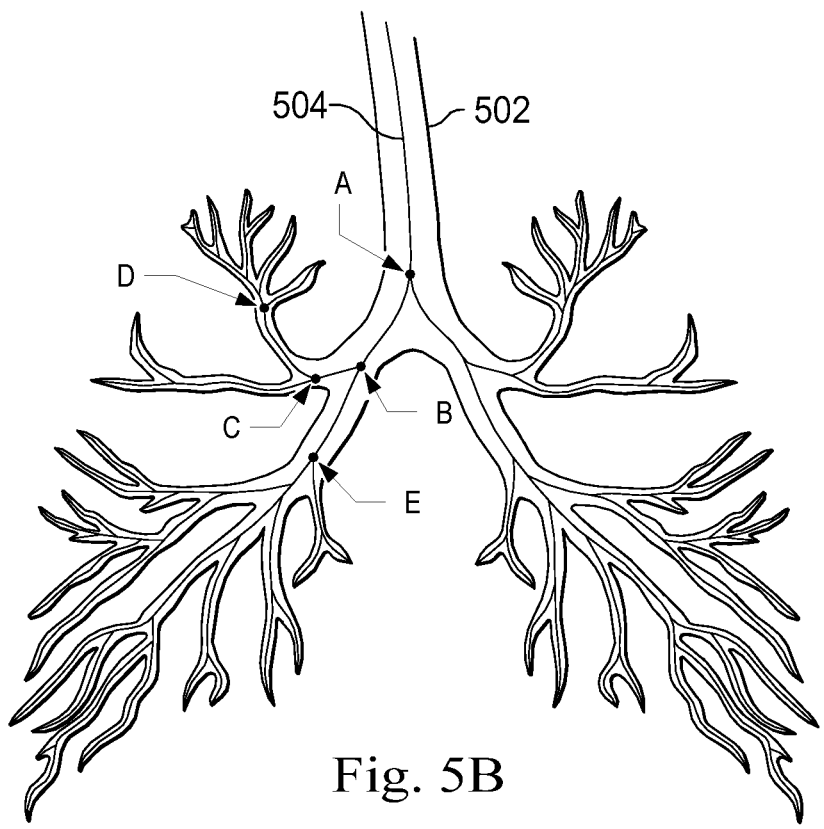
Figure 5C:
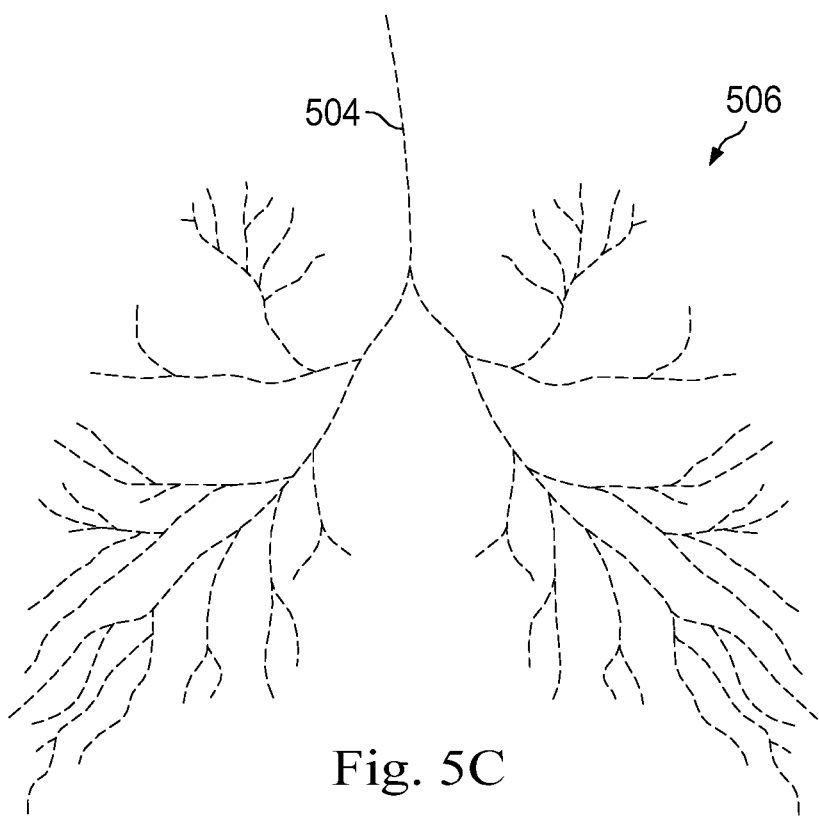

FIGS. 5A, 5B, and 5C illustrate steps in segmentation process that generates a model of a human lung for registration according to an embodiment of the present disclosure.

Figure 6A:
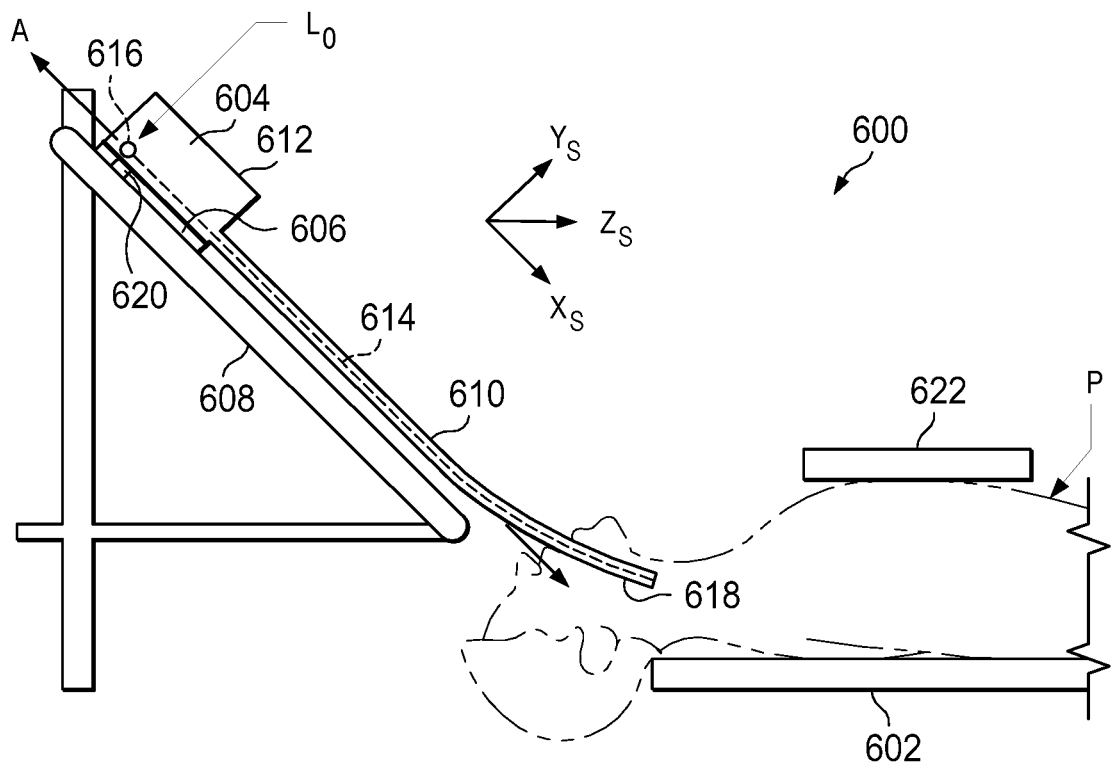
Figure 6B:
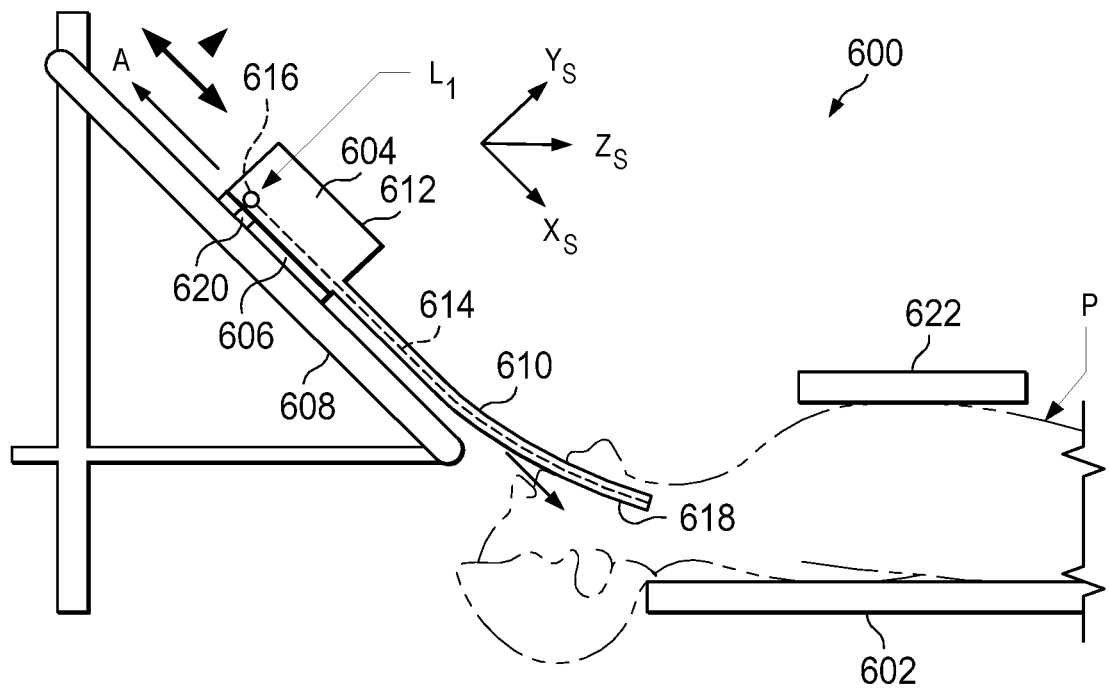

FIGS. 6A and 6B are side views of a patient coordinate space including a medical instrument mounted on an insertion assembly according to an embodiment of the present disclosure.

Figure 6C:
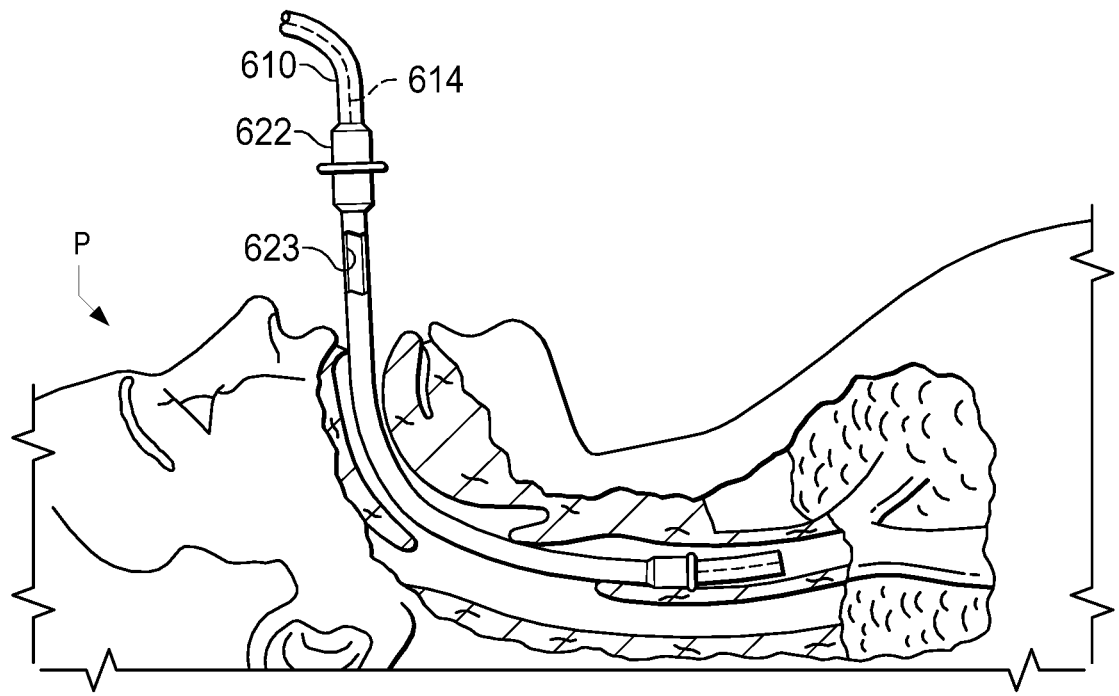

FIG. 6C is a side views of a patient in a patient coordinate space including an endotracheal tube according to an embodiment of the present disclosure.

Figure 6D:
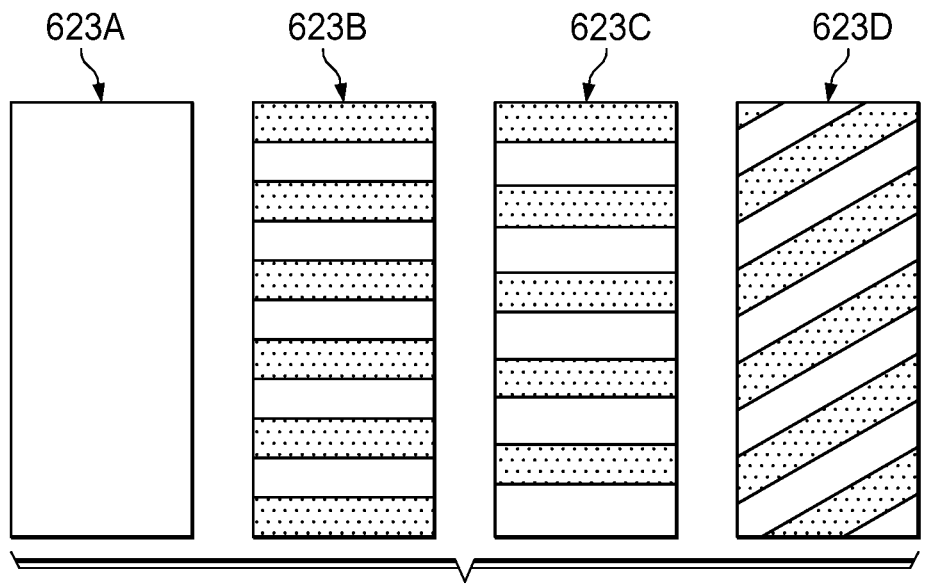

FIG. 6D includes diagrams of an interior surface of the endotracheal tube of FIG. according to aspects of the present disclosure.

Figure 7:
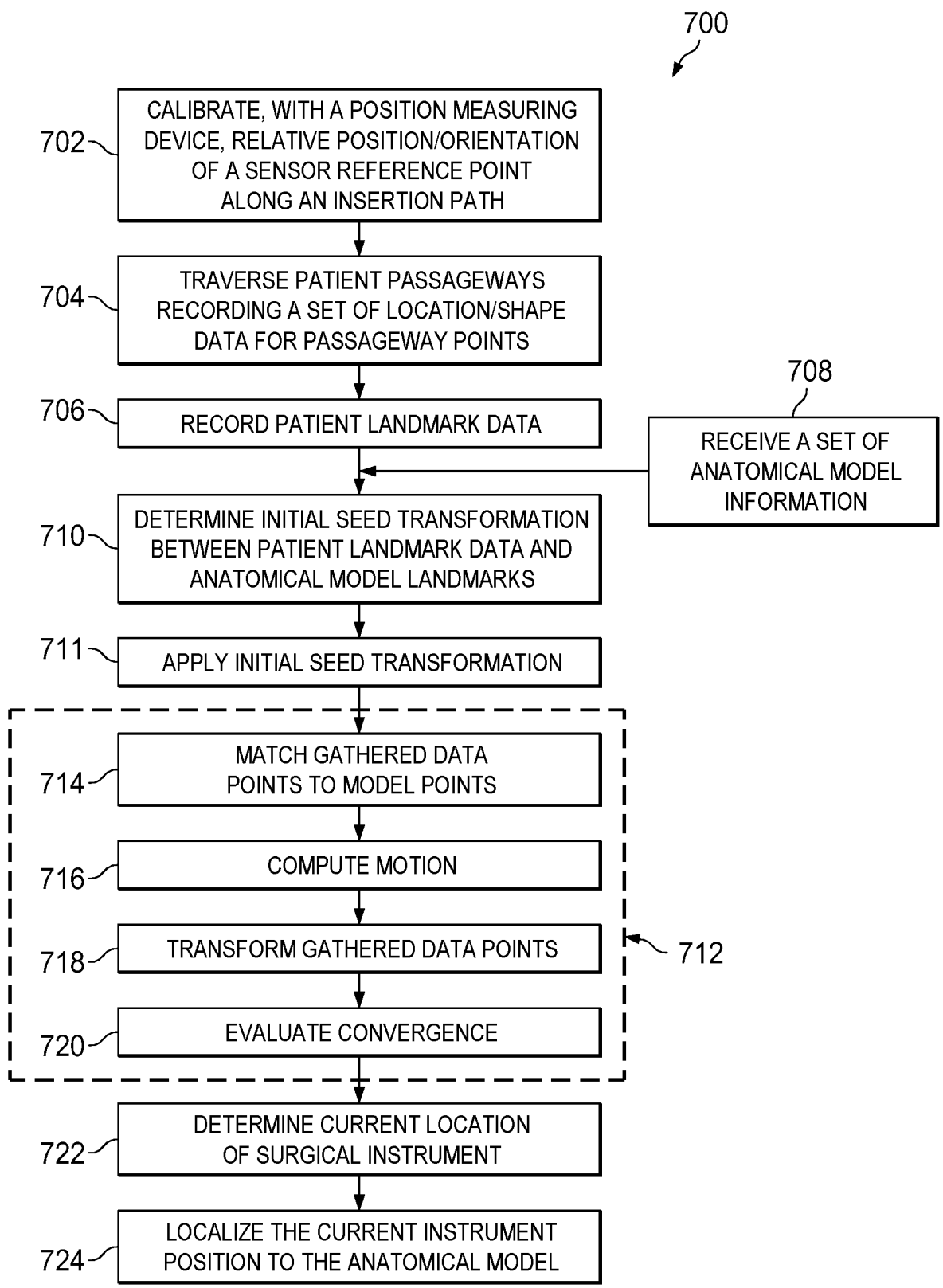

FIG. 7 illustrates a flowchart of a portion of an image-guided surgical procedure according to an embodiment of the present disclosure.

Figure 8:
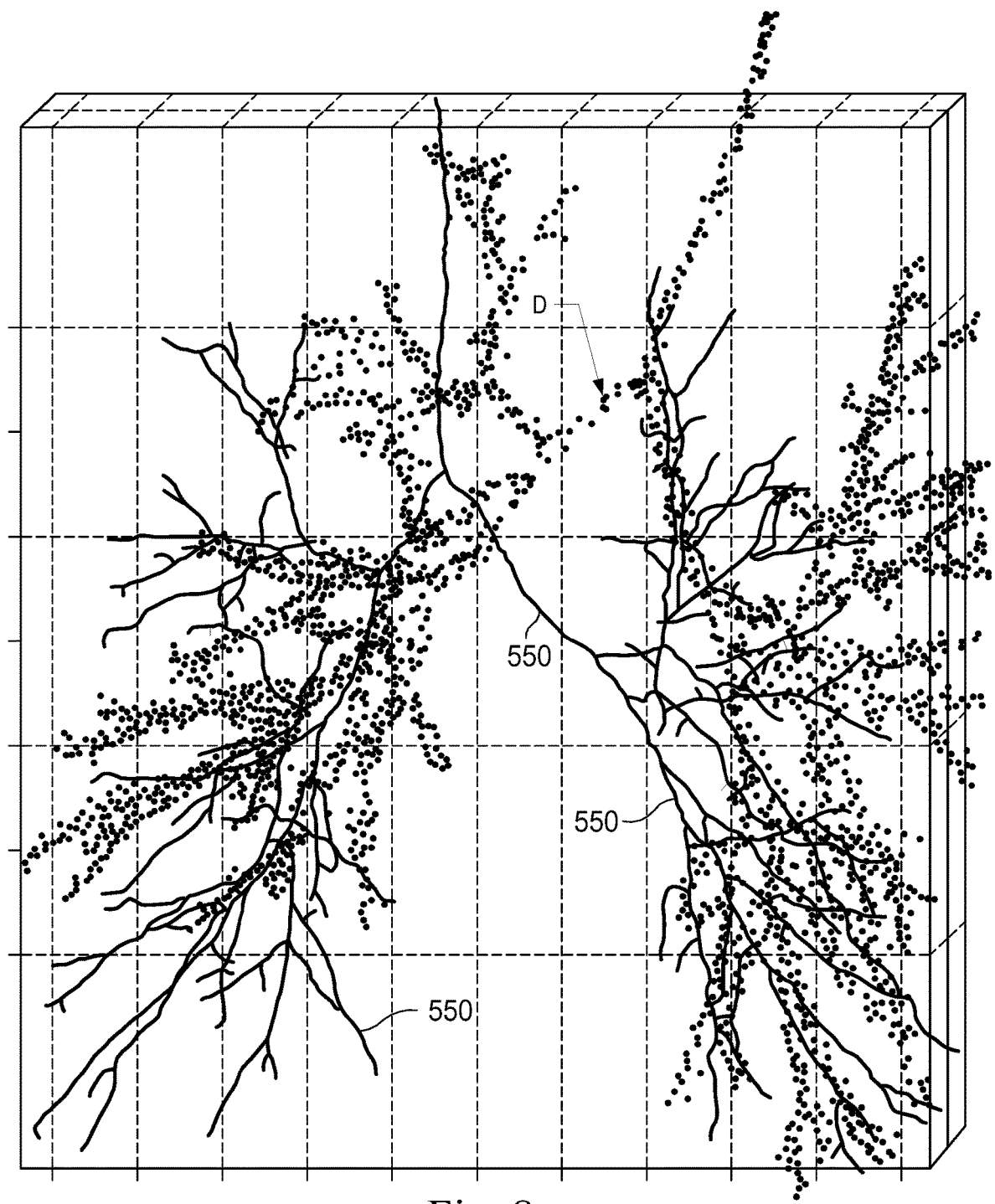

FIG. 8 illustrates two sets of points representing anatomy that are to be registered as part of an image-guided surgical according to an embodiment of the present disclosure.

Figure 9:
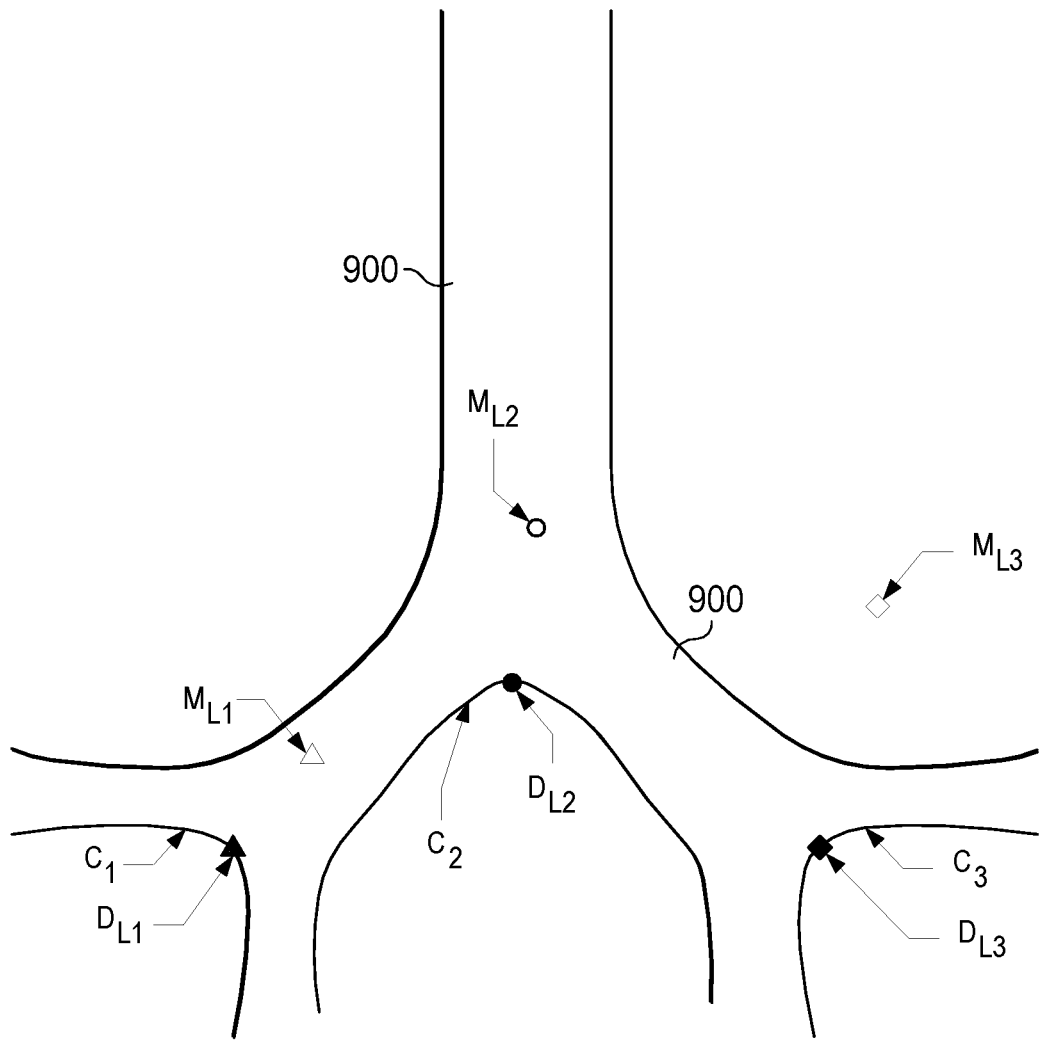

FIG. 9 illustrates a seeding process of an image-guided surgical procedure according to an embodiment of the present disclosure.

Figure 10:
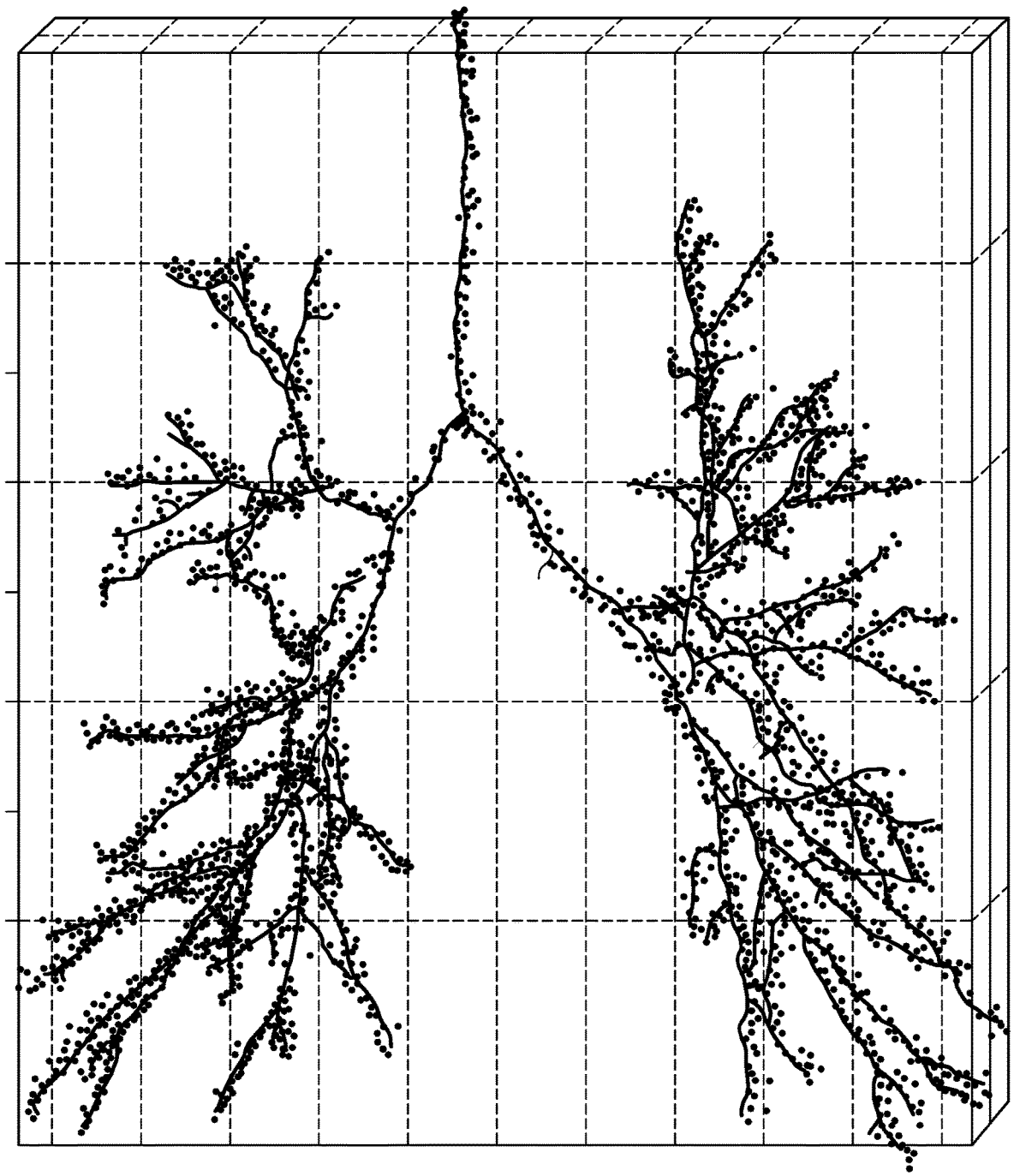

FIG. 10 illustrates a registration of the two sets of points resulting from a registration technique according to an embodiment of the present disclosure FIGS. 11A, 11B, 11C, 11D, 11E, 11F, 11G, and 11H illustrate various approaches for registering two sets of points representing patient anatomy according to embodiments of the present disclosure.

Figures 12, 13:
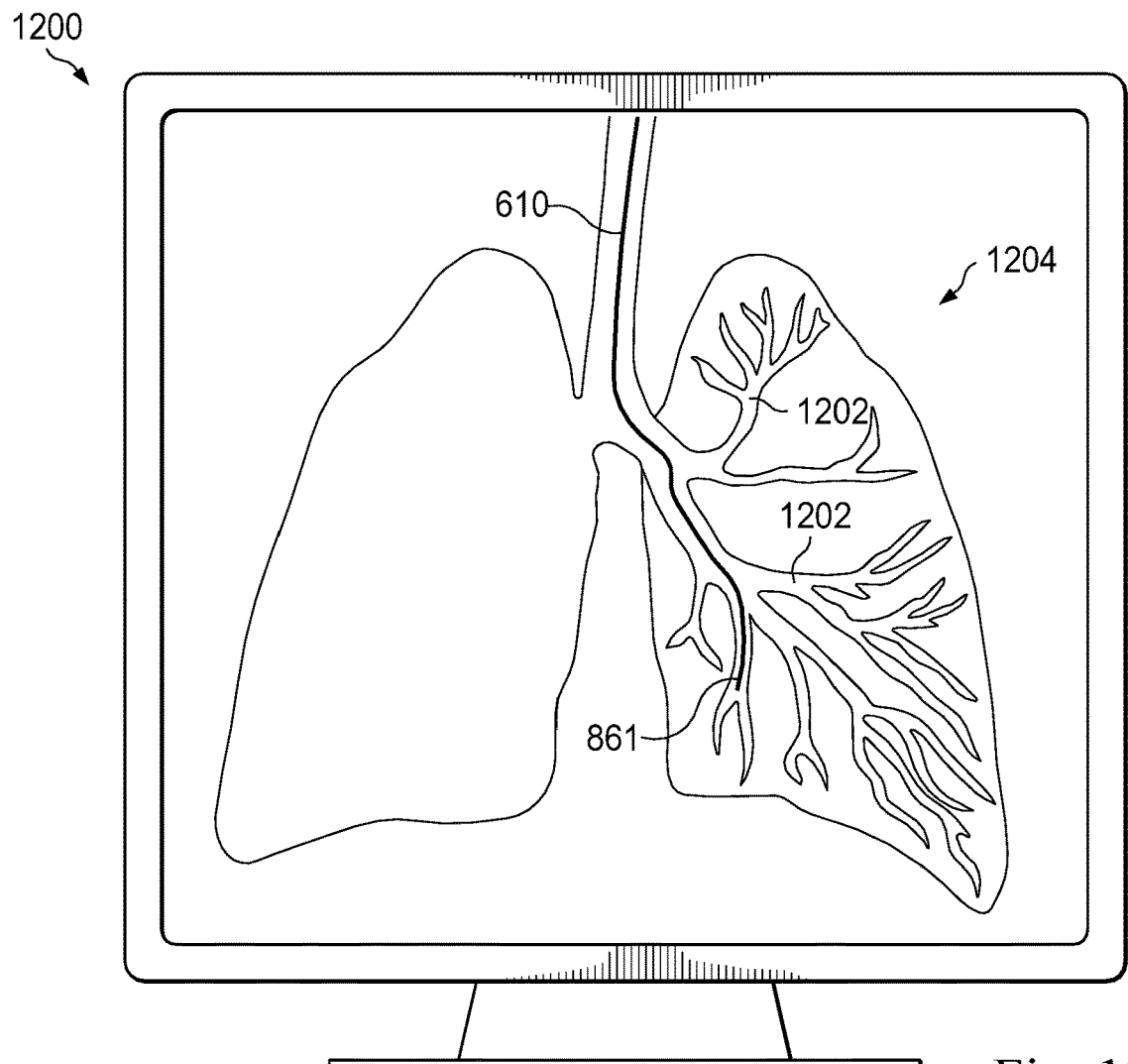

FIG. 12 illustrates a display stage of a registration technique according to an embodiment of the present disclosure.

FIG. 13 illustrates a point pool stored in memory according to an embodiment of the present disclosure.

Figure 14:
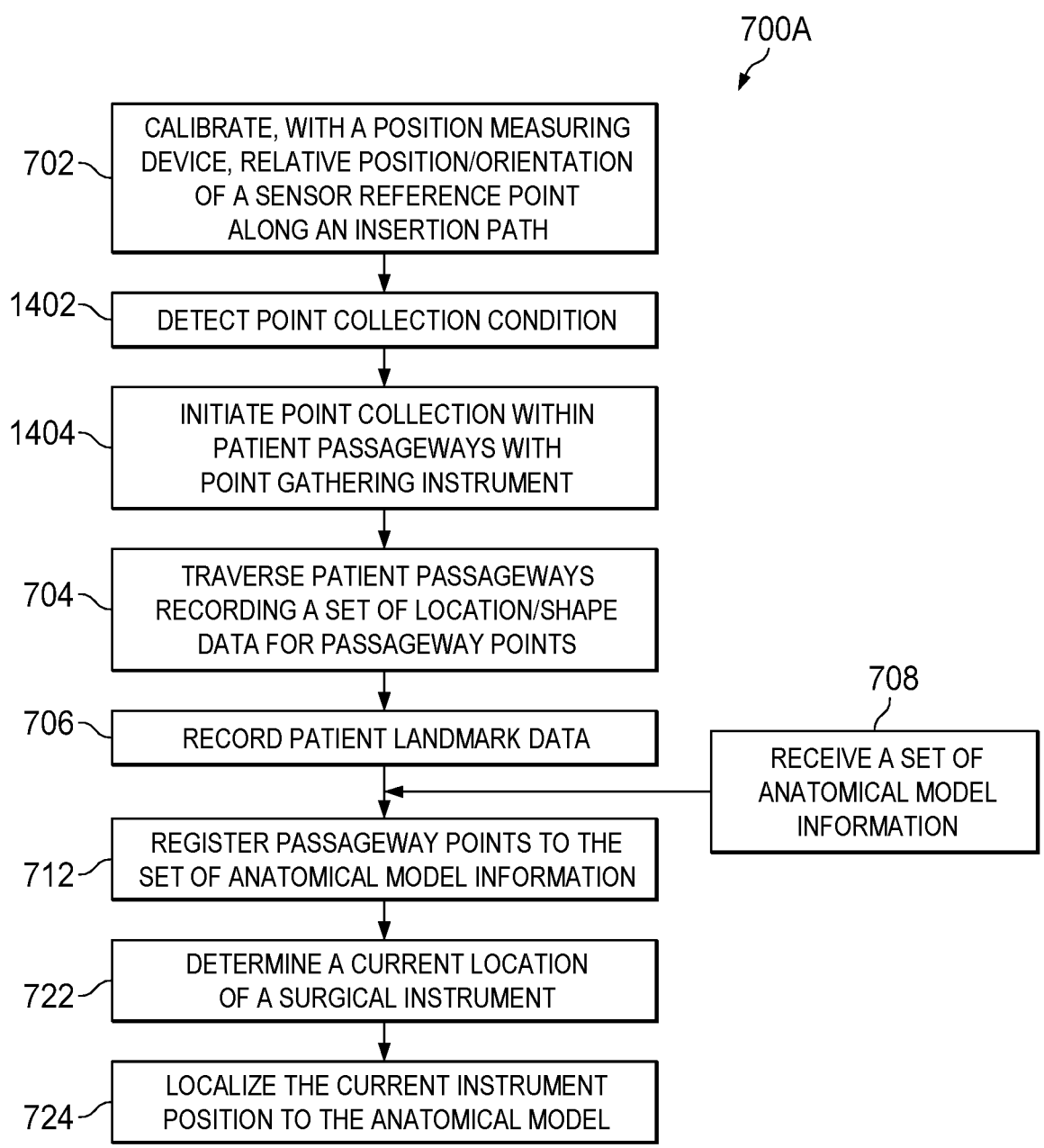

FIG. 14 illustrates a flowchart of a portion of an image-guided surgical procedure according to an embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
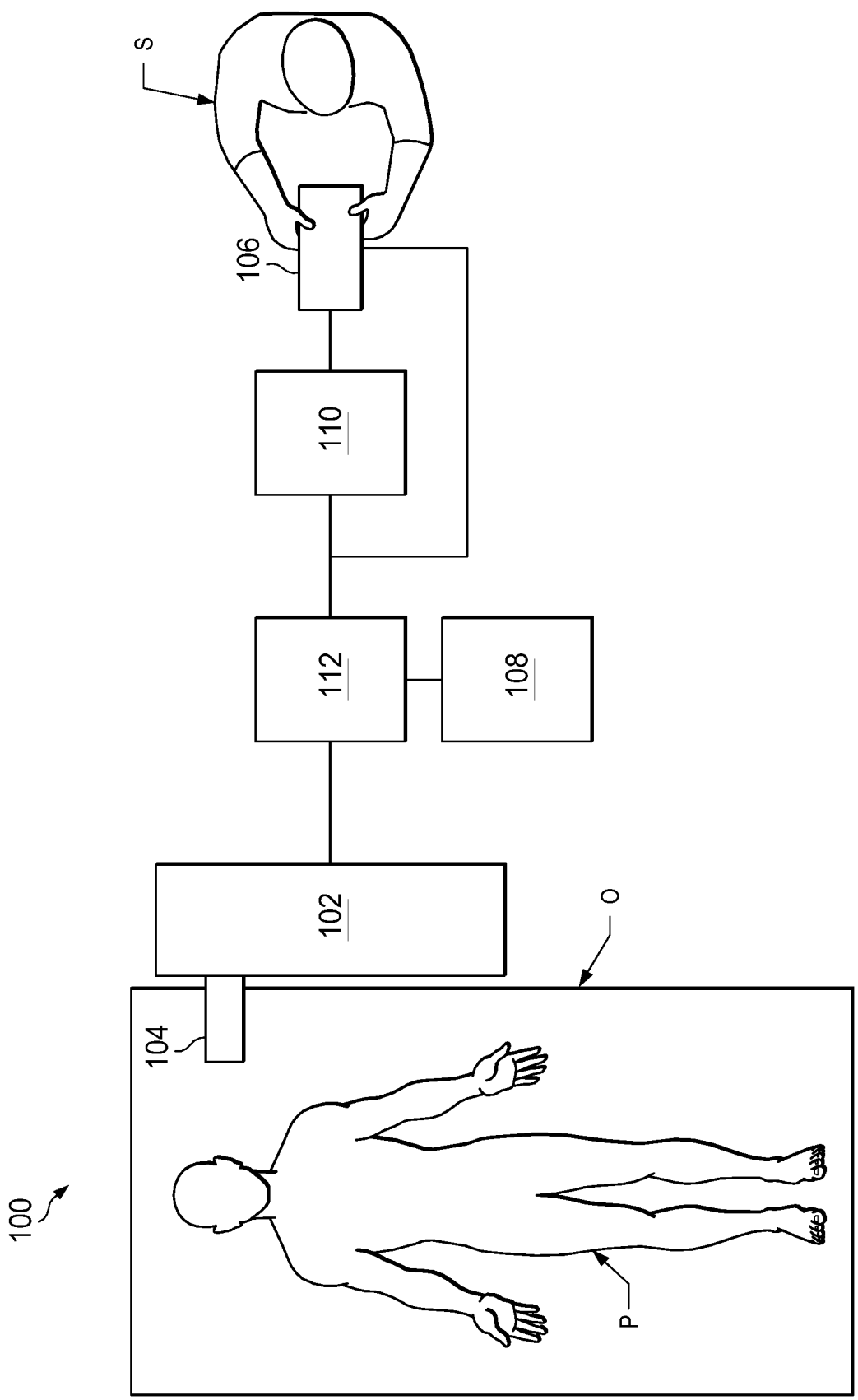
FIG. 1 is a teleoperated medical system, in accordance with embodiments of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a teleoperational manipulator assembly 102 for operating a medical instrument 104 in performing various procedures on the patient P. The assembly 102 is mounted to or near an operating table O. A master assembly 106 allows the clinician or surgeon S to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104. As described herein, visual representations of data points may be rendered to the display 110. For example, measured data points, moved data points, registered data points, and other data points described herein may be displayed on the display 110 in a visual representation. The data points may be visually represented in a user interface by a plurality of points or dots on the display or as a rendered model, such as a mesh or wire model created based on the set of data points. In some embodiments, a visual representation may be refreshed in the display 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomic passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using electromagnetic (EM) sensor, fiber optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2A:
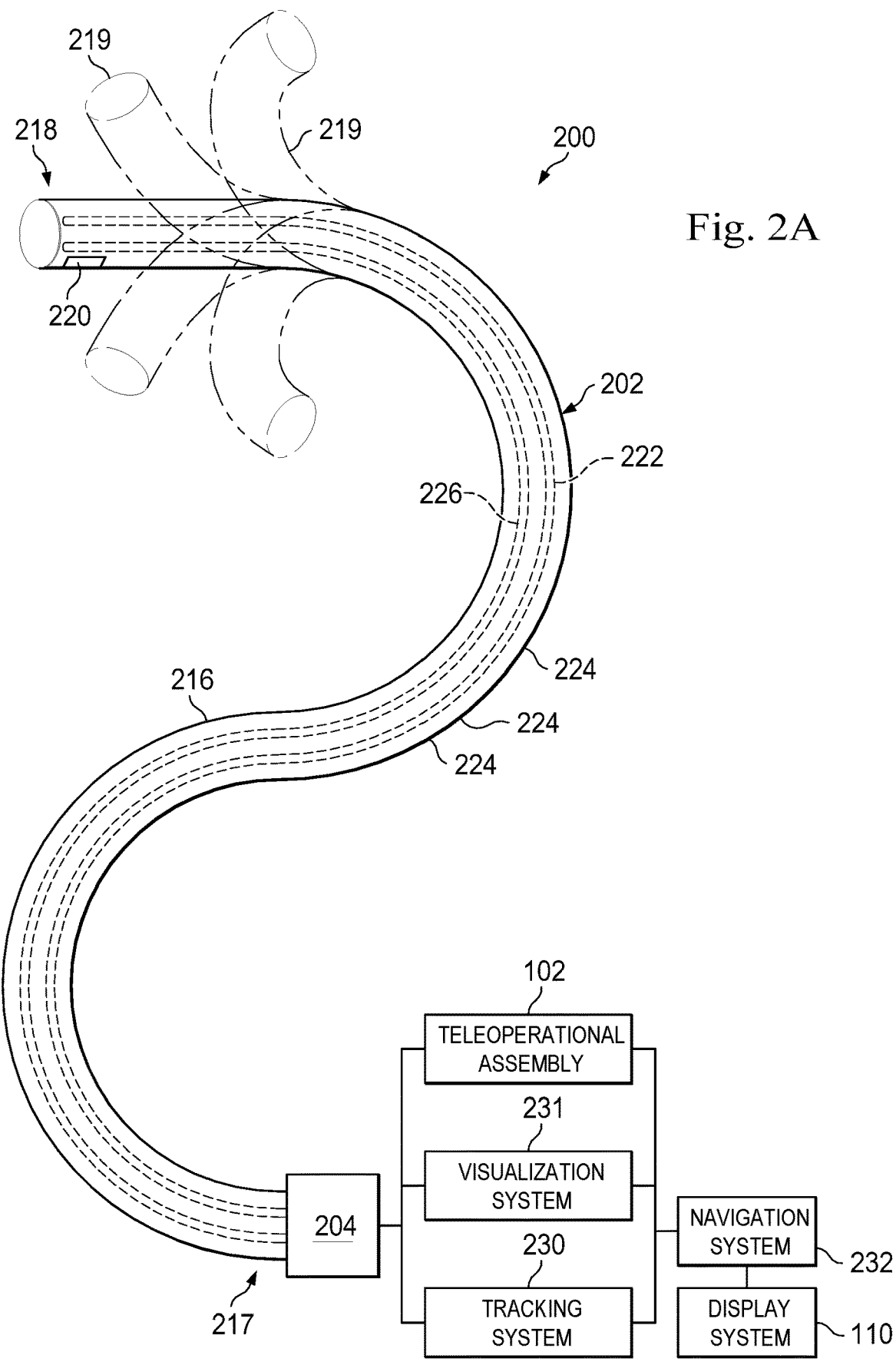
FIG. 2A illustrates a medical instrument system utilizing aspects of the present disclosure.

FIG. 2A illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In the embodiment of FIG. 2A, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 2B:
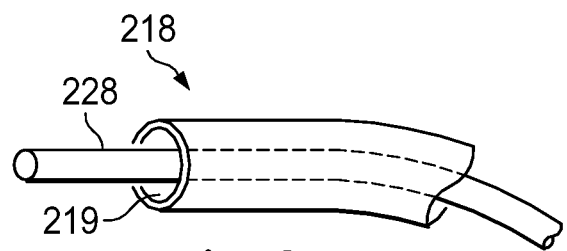
FIG. 2B illustrates a distal end of the medical instrument system of FIG. 2A with an extended medical tool, in accordance with embodiments of the present disclosure.

As shown in greater detail in FIG. 2B, medical tool(s) 228 for such procedures as surgery, biopsy, ablation, illumination, irrigation, or suction can be deployed through the channel 221 of the flexible body 216 and used at a target location within the anatomy. If, for example, the tool 228 is a biopsy instrument, it may be used to remove sample tissue or a sampling of cells from a target anatomic location. The medical tool 228 may be used with an image capture probe also within the flexible body 216. Alternatively, the tool 228 may itself be the image capture probe. The tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

Figure 3:
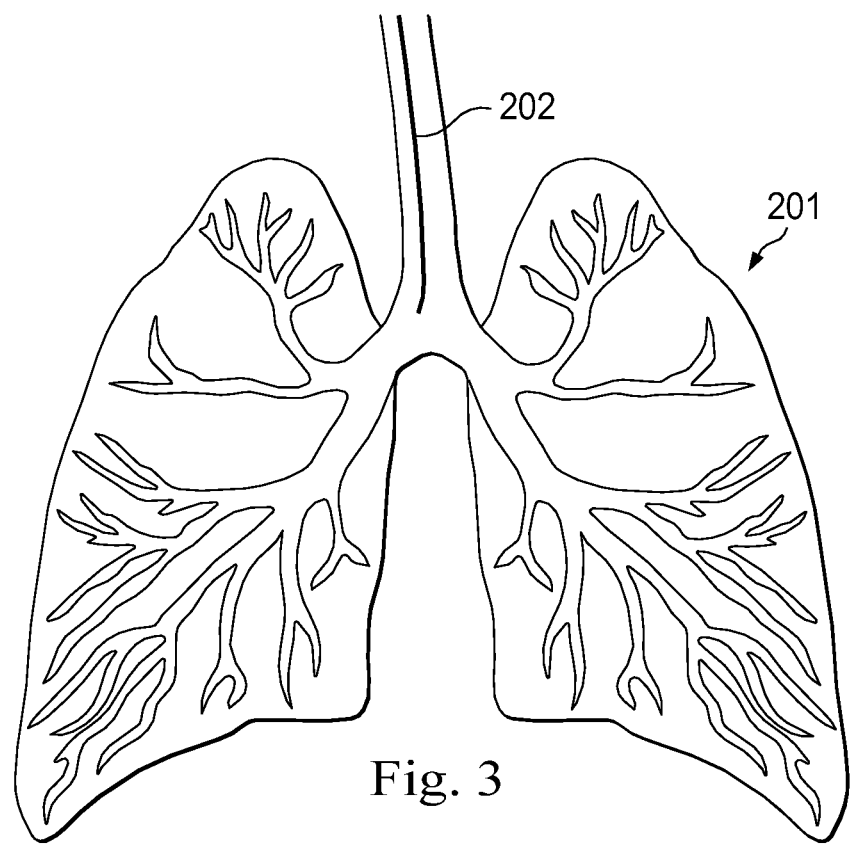
FIG. 3 illustrates the distal end of the medical instrument system of FIG. 2A positioned within a human lung.

FIG. 3 illustrates the catheter system 202 positioned within an anatomic passageway of a patient anatomy. In this embodiment, the anatomic passageway is an airway of human lungs 201. In alternative embodiments, the catheter system 202 may be used in other passageways of an anatomy.

Figure 4:
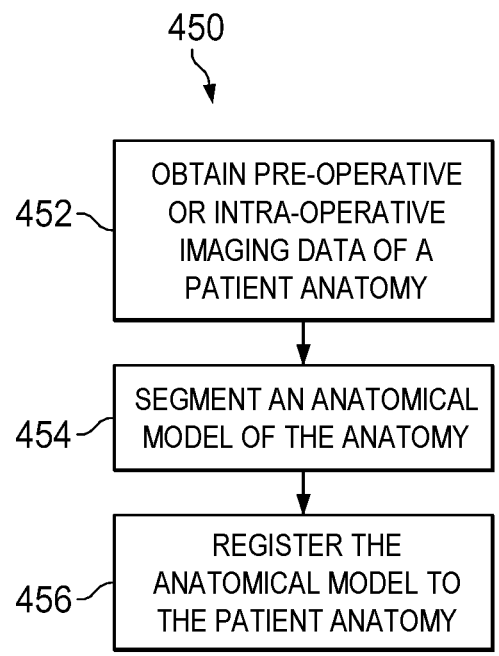
FIG. 4 is a flowchart illustrating a method used to provide guidance in an image-guided surgical procedure according to an embodiment of the present disclosure.

FIG. 4 is a flowchart illustrating a general method 450 for use in an image-guided surgical procedure. At a process 452, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 201 of FIG. 3. At a process 454, computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically. At a process 456, the anatomic model data is registered to the patient anatomy prior to and/or during the course of an image-guided surgical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique described in detail at FIG. 6 and elsewhere in this disclosure. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below perform registration based upon ICP, or another point set registration algorithm, and the calibrated movement of a point gathering instrument with a fiber optic shape sensor, thus eliminating or minimizing disruptions in the surgical environment. Other registration techniques may be used to register a set of measured points to a pre-operative model or a model obtained using another modality. In the embodiments described below, EM sensors on the patient and the instrument and optical tracking systems for the instrument may be eliminated.

FIGS. 5A, 5B, and 5C illustrate some of the steps of the general method 450 illustrated in FIG. 4. FIG. 5A illustrates a segmented model 502 of a set of anatomic passageways created from pre-operative or intra-operative imaging data. In this embodiment, the passageways are airways of a human lung. Due to naturally occurring limitations or to limitations set by an operator, the segmented model 502 may not include all of the passageways present within the human lungs. For example, relatively narrow and/or distal passageways of the lungs may not be fully included in the segmented model 502. The segment model 502 may be a three-dimensional model, such as a mesh model, that including the walls defining the interior lumens or passageways of the lungs.

Based on the segmented model 502, a centerline segmented model 504 may be generated as shown in FIG. 5B. The centerline segmented model 504 may include a set of three-dimensional straight lines or a set of curved lines that correspond to the approximate center of the passageways contained in the segmented model 502. The higher the resolution of the model, the more accurately the set of straight or curved lines will correspond to the center of the passageways. Representing the lungs with the centerline segmented model 504 may provide a smaller set of data that is more efficiently processed by one or more processors or processing cores than the data set of the segmented model 502, which represents the walls of the passageways. In this way the functioning of the control system 112 may be improved. As shown in FIG. 5B, the centerline segmented model 504 includes several branch points, some of which are highlighted for visibility in FIG. 5B. The branch points A, B, C, D, and E are shown at each of several of the branch points. The branch point A may represent the point in the model at which the trachea divides into the left and right principal bronchi. The right principal bronchus may be identified in the centerline segment model 504 as being located between branch points A and B. Similarly, secondary bronchi are identified by the branch points B and C and between the branch points B and E. Another generation may be defined between branch points C and D. Each of these generations may be associated with a representation of the diameter of the lumen of the corresponding passageway. In some embodiments, the centerline model 504 may include an average diameter value of each segmented generation. The average diameter value may be a patient-specific value or a more general value derived from multiple patients.

In other embodiments, the segemented model 502 may be used to produce the centerline segment 504 or another suitable model including a cloud, set, or collection of points as follows. When the segmented model 502 comprises a mesh representing the internal surfaces of one or more passageways, a subset of vertices of a mesh as represented in a stored data file including the model 502 may be used. Alternatively, a geometric center of voxels that represent volumes or the passageways in the segmented model 502 may be used. Additionally, combinations of various approaches may be used to generate a first set of points, such as the centerline segment model 504. For example, a subset of vertices of the mesh may be used along with the geometric center of voxels from the model.

In some embodiments, the centerline segmented model 504 is represented in data as a cloud, set, or collection of points in three-dimensional space, rather than as continuous lines. FIG. 5C illustrates the centerline segmented model 504 as a set of points 506. In data, each of the points of the set of model points may include coordinates such as a set of $X_M$, $Y_M$, and $Z_M$, coordinates, or other coordinates that identify the location of each point in the three-dimensional space. In some embodiments, each of the points may include a generation identifier that identifies which passageway generation the points are associated with and/or a diameter or radius value associated with that portion of the centerline segmented model 504. In some embodiments, information describing the radius or diameter associated with a given point may be provided as part of a separate data set.

After the centerline segmented model 504 is generated and stored in data as the set of points 506 shown in FIG. 5C, the centerline segmented model 504 may be retrieved from data storage for use in an image-guided surgical procedure. In order to use the centerline segmented model 504 in the image-guided surgical procedure, the model 504 may be registered to associate the modeled passageways in the model 504 with the patient's actual anatomy as present in a surgical environment. Use of the model 504 in point set registration includes using the set of points 506 from the model 504.

FIGS. 6A and 6B illustrate an exemplary surgical environment 600 according to some embodiments, with a surgical coordinate system $X_S$, $Y_S$, $Z_S$, in which a patient P is positioned on a platform 602. The patient P may be stationary within the surgical environment in the sense that gross patient movement is limited by sedation, restraint, or other means. Cyclic anatomic motion including respiration and cardiac motion of the patient P may continue, unless the patient is asked to hold his or her breath to temporarily suspend respiratory motion. Accordingly, data may be gathered at a specific, direction phase in respiration, and tagged and identified with that phase, in some embodiments. In other embodiments, the phase during which data is collected may be inferred from physiological information collected from the patient. Within the surgical environment 600, a point gathering instrument 604 is coupled to an instrument carriage 606. In various embodiments, the point gathering instrument 604 may use EM sensors, shape-sensors, and/or other sensor modalities. The instrument carriage 606 is mounted to an insertion stage 608 fixed within the surgical environment 600. Alternatively, the insertion stage 608 may be movable but have a known location (e.g., via a tracking sensor or other tracking device) within the surgical coordinate system. The instrument carriage 606 may be a component of a teleoperational manipulator assembly (e.g., assembly 102) that couples to the instrument 604 to control insertion motion (i.e. motion in an $X_S$ direction) and, optionally, motion of a distal end of the instrument in multiple directions including yaw, pitch, and roll. The instrument carriage 606 or the insertion stage 608 may include servomotors (not shown) that control motion of the instrument carriage along the insertion stage.

The point gathering instrument 604 may include a flexible catheter 610 coupled to a proximal rigid instrument body 612. The rigid instrument body 612 is coupled and fixed relative to the instrument carriage 606. In the illustrated embodiment, an optical fiber shape sensor 614 is fixed at a proximal point 616 on the rigid instrument body 612. In an alternative embodiment, the point 616 of the sensor 614 may be movable along the body 612 but the location of the point may be known (e.g., via a tracking sensor or other tracking device). The shape sensor 614 measures a shape from the point 616 to another point such as the distal end 618 of the catheter 610. The point gathering instrument 604 may be substantially similar to the medical instrument system 200.

A position measuring device 620 provides information about the position of the rigid instrument body 612 as it moves on the insertion stage 608 along an insertion axis A. The position measuring device 620 may include resolvers, encoders, potentiometers, and other mechanisms that determine the rotation and orientation of the motor shafts controlling the motion of the instrument carriage 606 and consequently the motion of the rigidly attached instrument body 612. In this embodiment, the insertion stage 608 is linear, but in alternative embodiments it may be curved or have a combination of curved and linear sections. Optionally, the linear track may be collapsible as described, for example, in U.S. Provisional Patent Application No. 62/029,917 (filed Jul. 28, 2014)(disclosing "Guide Apparatus For Delivery Of A Flexible Instrument And Methods Of Use") which is incorporated by reference herein in its entirety. FIG. 6A shows the instrument body 612 and carriage 606 in a retracted position along the insertion stage 608. In this retracted position, the proximal point 616 is at a position $L_0$ on the axis A. In this position along the insertion stage 608 an $X_S$ component of the location of the point 616 may be set to a zero or original value. With this retracted position of the instrument body 612 and carriage 606, the distal end 618 of the catheter may be positioned just inside an entry orifice of the patient P. Also in this position, the position measuring device may be set to a zero or original value (e.g. I=0). In FIG. 6B, the instrument body 612 and the carriage 606 have advanced along the linear track of the insertion stage 608 and the distal end of the catheter 610 has advanced into the patient P. In this advanced position, the proximal point 616 is at a position $L_1$ on the axis A.

Embodiments of the point gathering instrument 604 may collect measured points using any number of modalities, including EM sensing and shape-sensing. As the measurement points are collected from within the passageways of a patient, the points are stored in a data storage device, such as a memory. The set of measured points may be stored in a database that includes at least some, but may include all, of the measured points obtained during the procedure or immediately before the procedure. As stored in memory, each of the points may be represented by data comprising coordinates of the point, a timestamp, and a relative sensor position or individual sensor ID (when multiple sensors distributed along a length of the point gathering instrument 604 are used to determine the location of several points simultaneously). In some embodiments, data representing each point may also include a respiratory phase marker that indicates the respiratory phase of the patient in which the point was collected.

FIG. 7 is a flowchart illustrating a method 700 used to provide guidance to a clinician in an image-guided surgical procedure on the patient P in the surgical environment 600, according to an embodiment of the present disclosure. The method 700 is illustrated in FIG. 7 as a set of blocks, steps, operations, or processes. Not all of the illustrated, enumerated operations may be performed in all embodiments of the method 700. Additionally, some additional operations that are not expressly illustrated in FIG. 7 may be included before, after, in between, or as part of the enumerated processes. Some embodiments of the method 700 include instructions corresponded to the processes of the method 700 as stored in a memory. These instructions may be executed by a processor like a processor of the control system 112.

Thus, some embodiments of the method 700 may begin at a process 702, in which a calibration procedure is performed to calibrate, with a position measuring device like the point gathering instrument 604 or another suitable device, a relative position and/or orientation of a sensor reference point along an insertion path. For example, the point gathering instrument 604 of FIGS. 6A and 6B may be used to determine a position and orientation of the point 616 as the carriage 606 moves from a retracted position with the point 616 at location $L_0$ to an advanced position with the point 616 at the location $L_1$. The calibration procedure determines the direction of the movement of the point 616 for each change in the position measuring device 620. In this embodiment, where the insertion stage 608 restricts movement of the carriage 606 to a linear path, the calibration procedure determines the direction of the straight line. From the slope of the insertion stage track, the position and orientation of the point 616 in the surgical environment 600 may be determined for every corresponding measurement of the position measuring device 620. In an alternative embodiment, if the insertion stage has a curved or otherwise non-linear shape, the calibration procedure may determine the non-linear shape so that for every measurement of the position device, the position and orientation of the point 616 in the surgical environment may be determined. For example, the distal tip of the catheter may be held in a fixed position while the instrument body is routed along the non-linear insertion stage. The position and orientation data collected by the shape sensor from the fixed point 616 is correlated with the position measuring device data as the instrument body is routed along the insertion stage, thus calibrating movement of the point 616 along the axis A of the insertion stage 608.

At a process 704, the distal end 618 of the catheter 610 traverses the patient P's anatomic passageways (e.g., airways of the patient's lungs) recording, via data from the shape sensor 614, or another sensor such as an EM sensor or sensors provided on the catheter 610, location data for the distal end of the catheter and/or other points along the shape of the shape sensor. This location data may include, or be processed to obtain, a set of measured points as described herein. More specifically, the movement of the distal tip of the catheter 610 may be controlled via teleoperational, manual, or automated control (e.g., via master assembly 106) to survey a portion of the anatomic passageways.

For example, teleoperational control signals may cause the carriage 606 to move along the axis A, causing the distal tip 618 of the catheter to advance or retract within the anatomic passageways. Also or alternatively, teleoperational control signals may cause actuation of control members extending within the surgical instrument to move the distal tip 618 in a range of movements including yaw, pitch, and roll. As the catheter is moved within the plurality of passageways, shape sensor data (and/or other position data in other embodiments that do not include a sensor sensor) is gathered for multiple locations of the distal tip. In some embodiments, the catheter may extend up to approximately three inches into the various passageways. In some embodiments, the catheter may be extended through or into approximately three branched generations on each side of the lung. The number of generations accessible with the catheter 610 may increase as the diameter of the flexible catheter 610 decreases and/or the flexibility of the flexible catheter 610 increases.

With reference to FIG. 8, shape sensor data is gathered for a set of measured data points D, in some embodiments. These measured points may be stored in memory as data sets or point pools with coordinates, timestamps, sensor IDs, respiration phase information, etc., for each gathered point, as is discussed herein in connection with FIG. 13. This collected set of spatial information provided by data points D from the shape sensor or other point collection device may be gathered as the distal end 618 of the catheter 610 is moved to a plurality of locations within the surgical space 600. The location of a given collected data point $D_X$ in the surgical environment space 600 is determined by combining information from the position measuring device 620 when the distal end of the catheter is located at the point $D_X$ with the shape data from the shape sensor when the distal end of the catheter is located at the point $D_X$. Points may also be collected along the length of the catheter. In both such cases, the data from the position measuring device 620 and the calibrated path of the fixed sensor point 616 provides the position of the sensor point 616 in the patient surgical environment 600 when the distal end 618 of the catheter is at the point $D_X$. For example, encoder data from one or more motors controlling movement of the carriage 606 along the track 608 and the calibration data from the movement of the carriage along the track provides the position of the sensor point 616 in the surgical environment 600 when the distal end of the catheter is at the point $D_X$. The shape sensor provides the shape of the instrument between the fixed sensor point 616 and the distal end 618. Thus, the location of the point $D_X$ (where the distal end 618 is located) in the surgical environment space 600 can be determined from the calibrated position measuring data and the shape sensor data recorded when the distal end is at point $D_X$ and one or more points along the length of the shape sensor may be used to determine other points D as well. The location in the surgical environment 600 coordinate space for all of the data points D in the set of gathered data points (i.e. calibrated position of the proximal point 616 together combined with the shape sensor data for the location of the distal end 618 relative to the point 616) is a reference set of spatial information for the instrument that can be registered with anatomic model information.

Referring again to FIG. 7, at a process 706, one or more of the gathered data points D may correspond to landmark locations in the patient anatomy. In some embodiments, the gathered data points D that correspond to landmarks may be used to seed a registration process, such as an ICP process. In some embodiments of the method 700, the process 706 may not be performed and an automatic seed generation algorithm may be used in place of the process 706. Additionally, some embodiments of ICP processes may not include a seeding process. This subset of gathered data points D that correspond to one or more landmarks may be referred to as seed points. The data representing the subset of gathered data points D that correspond to landmarks may include a landmark indicator when stored in memory. With reference to FIG. 9, a set of anatomic passageways 900 includes main carinas $C_1$, $C_2$, $C_3$ where the passageways 900 fork. A data point D can be gathered for the location of each carina by moving the distal end of the catheter to the respective carina locations. For example, a data point $D_{L1}$ can be gathered at the carina $C_1$. A data point $D_{L2}$ can be gathered at the carina $C_2$. A data point $D_{L3}$ can be gathered at the carina $C_3$. The carinas or other suitable landmarks can be located in the patient surgical environment 600 as described above for point $D_X$.

Referring again to the method 700 of FIG. 7, at a process 708 anatomic model information is received. The anatomic model information may be the segmented centerline model 504 as described in FIG. 5C. Referring again to FIG. 9, the anatomic model information may be represented as a centerline model 550 of branched anatomic passageways. In some embodiments, the model may include one or more landmark points to match to the seed points $D_{L1}$, $D_{L2}$, and $D_{L3}$. These points included in the model to match to the seed points $D_{L1}$, $D_{L2}$, and $D_{L3}$ may not be centerline points in some embodiments, but may be included in the centerline model 550 to facilitate seeding of a subsequent registration process. In some embodiments, the centerline model 550 may include more model landmark points than $M_{L1}$, $M_{L2}$, and $M_{L3}$.

Referring again to FIG. 7, at a process 712 registration of the anatomic model information 550 with the set of gathered data points D from the surgical environment 600 is performed. Registration may be accomplished using a point set registration algorithm such as an iterative closest point (ICP) technique as described in processes 512-520, or by implementation of another registration algorithm. Prior to the process 712, at process 710, the ICP registration is seeded with known information about the displacement and orientation relationship between the patient surgical environment and the anatomic model. In this embodiment (FIG. 9), for example, the carina landmarks $C_1$, $C_2$, $C_3$ are identified in the anatomic model information as points $M_{L1}$, $M_{L2}$, $M_{L3}$. In alternative embodiments, the anatomic model information may be represented in other ways, e.g. as centerline segments or axes of a 3D mesh model. The recorded landmark data points $D_{L1}$, $D_{L2}$, and $D_{L3}$ from the patient surgical environment are each matched to a corresponding model points $M_{L1}$, $M_{L2}$, and $M_{L3}$. (i.e., $D_{L1}$ matches to $M_{L1}$, etc.) With the points matched, an initial transform (e.g., change in position and/or orientation) between landmark data points $D_{L1}$, $D_{L2}$, and $D_{L3}$ and model points $M_{L1}$, $M_{L2}$, and $M_{L3}$ is applied, at a process 711. This initial transform determined based on the landmark data points $D_{L1}$, $D_{L2}$, $D_{L3}$ and the model landmark points $M_{L1}$, $M_{L2}$, $M_{L3}$ may be applied to all of the gathered data points D. This seeding process, based on a few landmark points, provides an initial coarse registration of the gathered data points D to the anatomic model information 550.

The initial transform may be a rigid transform in which all landmark data points are transformed by the same change in position and orientation or may be a non-rigid transform in which the landmark data points are transformed by different changes in position and orientation. In some embodiments, in which the set of measured data points D undergoes rotation about at least one axis, the motion of each individual point may vary due to the placement of the axis or axes of rotation of the set of data points D.

The initial transformation performed at the seed stage can be performed based on many different model points and many different measured points. Similarly, the measured points used in the seed stage can be provided in many different ways. In some embodiments, multiple methods of seeding to providing the initial transformation are performed and each is checked for error. The method that provides the smallest error between the anatomic information model 550 and the set of points D may be used to begin the registration process.

For example, the major "Y" formation provided by the trachea and the left and right main bronchii shown in FIG. 9 may be used as explained herein. Each of the first three main bifurcation points or carinas $C_1$, $C_2$, and $C_3$ may be identified in the model and in the set of data points D. In some embodiments, the process of collecting data points D may cause an identifier to be included as part of the recorded data for certain points to be used in the seeding process to be included in data for that point. This identifier may be included automatically as part of a workflow or a clinician controlling the point gathering instrument 604 may use an interface to manually indicate, by clicking a button for example, that a point defined by the distal end 618 of the catheter 610 point gathering instrument 604 at a specific time is to be used in the seeding process (i.e., is a landmark data point). For example, after inserting the catheter the clinician may position the distal end 618 at the carina $C_2$ and click a button to capture the location as a data point $D_{L2}$. The clinician may then navigate, in some embodiments using an image sensor positioned within the passageways of the patient P, to the carina $C_1$ and click the button to capture the location as the data point $D_{L1}$. The clinician may then navigate to the carina $C_3$ and click the button to capture the location as the data point $D_{L3}$. In some embodiments, the interface of a medical system may direct the clinician to navigate to a specific location and then affirm through the manipulation of an interface element that the distal end 618 is at the specific location, at which point the corresponding data point is collected. The data points gathered in this way may include coordinates and other information described herein and may further include an indication that the data points are seed points or landmark points that can be used in the seeding process to perform the initial coarse transformation.

Other user interface interactions may be used to trigger the collection of a data point $D_X$ or data points $D_X$ for use in the seeding process. For example, where the medical system includes a voice recognition component, the clinician may speak aloud to identify a present location of the distal end 618 as a seed point or to confirm a collected point as a seed point corresponding to a specific location requested by a workflow. While in the example above a workflow is provided by the medical system to collect the data points $D_{L1}$, $D_{L2}$, $D_{L3}$ for use in the seeding process, in other embodiments a user may pick preferred landmarks, including landmarks other than the main carinas as shown in FIG. 9. Through the user interface, the clinician may identify the anatomic location of the selected landmarks so that a corresponding location in the anatomic model information may be approximated.

In some embodiments, sensors provided at the distal or proximal end of the catheter 610 may be used to trigger the collection of data points including data points $D_{L1}$, $D_{L2}$, and $D_{L3}$ for use in the seeding process. For example, as part of a workflow the medical system may use the first three collected data points $D_{X1}$, $D_{X2}$, and $D_{X3}$. In such an embodiment, the clinician may navigate to the main carina $C_1$ and cause physical contact between the main carina $C_1$ and the distal end 618. A torque sensor or an encoder for actuator controlling the distal end of the catheter may register resistance or a force against the distal end and trigger the collection of the data point $D_{L1}$ in response.

In some embodiments, a touch sensor such as a capacitive or Hall effect sensor may be positioned along the flexible instrument to provide an indication when the instrument is close to or in contact with a wall of the anatomic passageway. Thus, the touch sensor may provide information about the shape and size of passageways that may be used to identify corresponding characteristics in the model data.

While the main carinas may be used in the seeding process for some embodiments, other embodiments may rely on other anatomic features to perform the initial registration. For example, when the distal end 618 of the catheter 610 is passed through an endotracheal (ET) tube used to guide the catheter 610 through the mouth of the patient P the catheter 610 may conform to a known bend or curve corresponding to the endotracheal tube. An exemplary ET tube 622 is illustrated in FIGS. 6C and 6D. Even if a bend 621 in the tube is not precisely known, the curvature may be sufficiently distinctive to be identified as corresponding to the upper respiratory track and trachea because the portion of the catheter 610 at the proximal end of the ET tube 622 forms a nearly 90° angle with respect to the portion of the catheter 610 at the distal end of the ET tube 622. The pose of the proximal end of the point gathering instrument may be known due to sensors in the joints of the teleoperational assembly 102. Based on this pose information and a curve of the endotracheal tube, which may be easily identified using shape sensor data, the trachea of the patient P may be identified and used to seed an initial transformation. While the orientation of the patient P to the point gathering instrument 604 may already be known, by navigating the distal end 618 into either the left or right primary bronchus (shown in FIG. 6C) additional information may be gathered that can be used to seed the initial transformation. For example, using shape sensor or EM sensor data, information characterizing a first roughly right angle may be collected between the entrance of the ET tube and exit of the ET tube into the length of the trachea of the patient P. This first angle may identify a plane that may be expected to bisect the anatomic model information 550. When the distal end 618 transitions from the trachea into either the left or right primary bronchus, a second angle defining a second plane may be identified. The first and second places are roughly orthogonal. By using the first and second angles, the medical system may identify a right-left orientation of the patient which may be used to seed the registration process by roughly orienting the data points D with the anatomic model information 550.

Referring again to FIG. 6C, shown therein is a close-up view of the patient P as shown in the FIGS. 6A and 6B. FIG. 6C illustrates an ET tube 622 positioned within the patient P to guide the catheter 610 into the patient P's lungs. The ET tube 622 includes an interior surface 623 that may include a distinctive color and/or a distinctive pattern.

In embodiments in which an endoscopic camera is incorporated into or used in conjunction with the point gathering instrument 604, image information may also be used to provide a seed. For example, image data may be used by the medical system to determine whether or not the catheter 610 is in the trachea, or another passageway, of the patient P. This may be done, for example, by using a camera to monitor for a change in anatomic color, texture, or anatomic feature associated with changes in anatomic region (e.g., the entrance of to the trachea). Alternatively, the camera may be used to monitor for a change in color or pattern of the interior surface 623 of the ET tube 622 or the movement of the camera past a distal end of the ET tube which terminates in the trachea.

To facilitate the detection of the catheter 610 entering and/or exiting the ET tube, the ET tube may include a distinguishing color, marking, and/or pattern. For example, the ET tube may be bright green, orange, or another color. In some embodiments, the ET tube may include markings such as symbols or alphanumeric characters. In some embodiments, the ET tube may include a pattern such as a striped pattern alternating between a bright color and dark color. Additionally, in some embodiments, the ET tube 622 may be coated with a reflective coating. Based on the color, marking, and/or pattern of ET tube, the medical system may use images obtained by the camera to determine whether the distal end 618 is within the ET tube or has exited into the trachea. Examples of the interior surface 623 are illustrated in FIG. 6D. The colors, markings, and/or patterns may also be captured in the pre-operative or intra-operative imaging data and thus serve as fiducial markers in the seeding procedure.

As shown in FIG. 6D, the interior surface 623A has a solid color. The solid color may be a hunter orange, a fluorescent green, or any color that is readily distinct to machine vision when compared with the naturally occurring colors of the passageways of the patient P. The interior surface 623B shows a pattern including alternating stripes of at least two colors. For example, black and white stripes may be used in some embodiments. While the stripes of the interior surface 623B are all equal, the stripes of the interior surface 623C may include stripes of different widths. As shown the light stripes increase in width, while the dark stripes have a common width. In some embodiment both the light and dark stripes may vary in width along the length of the ET tube 622. While the stripes of interior surface 623B and 623C are arranged orthogonally to a central axis of the ET tube 622, the interior surface 623D includes stripes that are not orthogonal to the central axis. The surface 623D includes alternating strips oblique to the central axis. In alternative embodiments, the colors, markings, or patterns may change along the length of the surface 623 to provide an indication of the insertion depth of the camera.

In other embodiments the pose of the catheter 610 may be estimated based on an endoscopic image by comparing an expected position to an actual image. For example, a camera image of the main carina during insertion of a medical instrument, such as an endoscope, may be compared to a virtual segmented representation of the main carina and used to estimate insertion depth and roll angle of the endoscope. The roll angle may have two possible solutions 180° apart corresponding to the left and right main bronchii of the patient. In such an instance, two registration processes could be initiated, one for each of the possible solutions. The registration that provides the better result could be maintained and continued while the other registration could be discarded.

Referring again to the method 700 of FIG. 7, at a process 714 with the initial coarse transformation performed to initiate the registration process, the set of measured data points D gathered from within the patient P is matched to the anatomic model information 550 (FIG. 10). For example, each of the measured data points D may be matched with the closest point in the anatomic model information 550. In this embodiment, the anatomic model information 550 is a set of points along the centerlines generated from a three-dimensional anatomic model, like the segmented centerline model 504 is generated from the segmented model 502 of FIG. 5C. The registration algorithm identifies matches between closest points in the gathered data points D and in the set of anatomic model points. In various alternatives, matching may be accomplished by using brute force techniques, KD tree techniques, etc. Some matches may be discarded based on maximum distance threshold calculations, maximum angle threshold calculations, or other metrics employed to filter out matches that are not deemed to be reliable enough for inclusion in the model. The anatomic model points may be represented by any of several different kinds of points, including centerline points, mesh points, and/or volume points. In some embodiments, only a subset of measured data points D are matched with the set of points in the anatomic model. Multiple heuristics may be implemented to determine which of the measured data points D are included in the subset of measured points.

At a process 716, the motion needed to move the set of gathered data points D to the position and orientation of the matched anatomic model points of the anatomic model information 550 is determined. More specifically, an overall computed offset in position and orientation is determined for the set of gathered data points D. FIG. 8, for example, illustrates an initial offset of approximately 20° in orientation and 40 mm in displacement between the gathered data points D and the anatomic model information 550. In some embodiments, the computed corrective motion may be limited such that only a certain number of degrees of rotation for a certain number of millimeters of displacement may be applied in a single iteration of the process 712. In some embodiments, even if a rotation or reorientation of the anatomic model information 550 of 20° is computed, the medical system may limit the change in orientation to 10°, 5°, or less. Similarly, in some embodiments even if a displacement of 40 mm is computed, the medical system may limit the displacement available in a single iteration to 20 mm, 10 mm, 5 mm, or less. In some embodiments, the limits may change according to a number of iterations performed such that less movement is permitted in later iterations than in earlier iterations.

At a process 718, the set of gathered data points D are transformed using a rigid or non-rigid transformation that applies the computed offset in displacement and orientation to move each point in the set of gathered data points D. A limited computed offset may be applied if the computed offset is greater than establish limits. In an alternative embodiment, the modeled data points may be transformed by using a rigid or non-rigid transform that applies the computed offset in displacement and orientation to move each point in the set of modeled data points 550 toward the gathered data points D. Accordingly, some embodiments of the present disclosure may refer to registering measured points to model points and moving (including translating and/or changing the orientation of) the measured points to better align with the model points. These embodiments also encompass registering measured points to model points and reorienting the model points to better align with the measured points. In still another alternative embodiment, the computed offset may be partially applied to the set of gathered data points D and partially applied to the modeled data points 550 such that both sets of points are transformed to converge in a common frame of reference distinct from either the frame of the gathered data points or the frame of the modeled data points.

At a process 720, the convergence of the gathered data points D and the matched anatomic model points 550 is evaluated. In other words, error factors for orientation and displacement may be determined for each matched point set. If the error factors in aggregate are greater than a threshold value, additional iterations of processes 714-720 may be repeated until the overall position and orientation error factors falls below the threshold value. A result of this process is illustrated in FIG. 10. The result shown in FIG. 10 may represent the result of repeating the processes 712 for multiple iterations. For example, more than 50 iterations may be performed to converge on a satisfactory registration. However, fewer than 30 iterations may be needed to achieve a satisfactory registration, in some embodiments. The registration process including seeding and the processes 712 may be understood as orienting a set of anatomic model information 550 to a set of points D present in space defined by a surgical environment; as orienting the set of points D to a set of anatomic model information 550 in an anatomic model space; or as orienting both sets of points D and anatomic model points 550 to a common space distinct from the surgical environment or the model space.

The sum of the computed motions required to minimize the error between the set of measured points D and anatomic model information 550 may be applied to a model having greater detail than is present in the anatomic model information 550. For example, after registering the segmented centerline model 504 of FIG. 5C, the same transformation may be applied for another model such as the segmented model 502 of FIG. 5A. Thereafter, a clinician may be presented with a user interface that displays both of the segmented model 502 or portions thereof and live information such as the current position of a catheter within the passageways of a long of patient P. The segmented model 502 and the live information may be presented in separate windows or screens or may be overlaid and presented jointly in a single window.

The registration process 712 may be recomputed multiple times during a surgical procedure (e.g., once every ten second, once every minute, once every five minutes, etc.) periodically and/or in response to deformation of the passageways caused by cyclic anatomic motion, instrument forces, and/or other changes in the patient environment or in the patient's orientation to the environment, such as by a patient movement.

After the anatomic model is registered to the surgical environment, an image-guided surgical procedure may, optionally, be performed. The anatomic model may include previously captured details from modalities that are difficult to use during a surgical procedure and so are generally captured pre-operatively. Referring again to FIG. 8, at process 722, during a surgical procedure, a current location of a surgical instrument in the surgical environment is determined. For example, the position of the surgical instrument, and particularly the distal end 618, in the surgical environment 600 may be determined using position sensors such as EM sensors. Alternatively, the data from the position measuring device 620 and the calibrated path of the fixed sensor point 616 provides the position of the sensor point 616 in the patient surgical environment 600 when the catheter is in a current location. The shape sensor or multiple discrete sensors provide the shape of the instrument between the fixed sensor point 616 and the distal end 618. Thus, the current location of the catheter 610 and, particularly, the distal end 618 of the catheter in the surgical environment space 600 can be determined from the calibrated position measuring data and the shape sensor data.

At process 724, the previously determined registration transforms are applied to the current instrument position and shape data to localize the current instrument to the anatomic model. For example, the current position and orientation for the distal end of the instrument, data point $D_{current}$ is transformed using the one or more transform iterations determined at process 712. Thus, the data point $D_{current}$ in the surgical environment 600 is transformed to the anatomic model space. Alternatively, if the model data points have been transformed to the surgical environment 600 and the catheter 610 is localized in the surgical environment, process 724 may be omitted.

Optionally, the registration allows for the presentation of one or more images to assist with an image guided procedure. For example, an image of the catheter superimposed on the segmented model passageways may be presented. Additionally or alternatively, an internal image of the anatomic passageways within the model from the perspective of the localized distal end of the catheter (i.e. a view just distal of the distal end 618) may be presented.

Referring now to FIGS. 11A-H, shown therein are several different rules or heuristics that may be used in selecting a subset of measured data points D that are then used to match to an anatomic model to compute a corrective motion. By identifying points that include superior information and ignoring points that include inferior information, a control system performing registration may operate more efficiently. Increased efficiency may permit the periodic or event driven updating of a registration or re-registration with minimal delay in the presentation of images used for surgical navigation. In some embodiments, only a subset of measured data points is used in the matching process 714. A set of measured data points 1102 are shown as they relate to an anatomic model 1104, illustrated as a collection of segments 1104A-G. While the segments 1104A-G of the anatomic model 1104 are illustrated as lines in FIGS. 11A-H, these segments 1104A-G may also correspond to collections of model points (including points 1106A-F) extending along the center of the passageways of a lung or other organ with passageways.

As shown in FIG. 11A, the set of measured data points 1102 exhibit a general correlation to the segments of the anatomic model 1104. This correlation may be a result of previous iterations of the registration process or of the seeding of such registration process. When computing a corrective motion by which to transform the measured points 1102 to better align with the anatomic model 1104, multiple error values may be obtained as part of the process of computing the motion. In some embodiments, these error values may be distances between matched points. In general, the smallest error value associated with a specific measured data point may be a match.

As illustrated in FIG. 11A, the measured data point 1102A matches to a model point 1106A. A distance 1107 characterizes a distance or error value associated with the matched pair of the measured data point 1102A and the model point 1106A. These points may be matched because the distance 1107 is the shortest distance between the measured data point 1102A and any other model point in the anatomic model 1104. Other matches illustrated in FIG. 11A include a match between the measured point 1102B and model point 1106B, another match between the measured point 1102C and model point 1106C, and another match between the measured point 1102D and model point 1106D. The measured point 1102D is also matched with the model point 1106E. The distance between the measured point 1102D and the model point 1106D and the distance between the measured point 1102D and the model point 1106E may be identical or may be substantially similar so as to be considered identical. For example, when the distances between a measured point and two model points differ by less than a threshold percentage (e.g., 10%, 5%, 3%, etc.), the distances may be deemed identical for certain purposes. In some embodiments, the distance between the model points 1106D and 1106E may be calculated, and, as a heuristic, both the matches may be discarded when the distance between the model points is greater than the distance between either of the model points and the measured point 1102D as this may be an indication that the two matches are associated with different airways. When the distance between the model points is less than a distance between either of the model points and the measured point, the matches may be averaged or a single match may be selected. When multiple measured points match to a single model point, the measured points may be averaged to create a single averaged point.

In order to more efficiently and/or accurately register the measured data points 1102 with the anatomic model 1104, the effect of some points may be ignored based on one or more heuristics during the computation of the corrective motion. Matching saliency may be the basis for ignoring or discarding a measured point. For example, because the measured point 1102D is effectively matched to both the model points 1106D and 1106E, the matches may be ignored when calculating the corrective motion. This may be done by ignoring the measured point 1102D. When ignoring a measured point in the various algorithms disclosed herein, the measured point may be temporarily ignored. For example, the measured point 1102D and its associated matches with the model points 1106D and 1106E may not be factored into the corrective motion as determined in one iteration, but may be factored into the corrective motions determined in subsequent iterations. Alternatively, a measured point may be deleted permanently rather than temporarily.

The measured data point 1102C matches to the model point 1106C. The model point 1106C is a "terminal point" in that it is the most distal point in the segment 1104G, a segment that does not connect to a subsequent segment at its distal end. In some embodiments, a heuristic provides that measured points that match to a terminal point of the model are ignored at least for one iteration. As shown in FIG. 11A, the match between the point 1102C and the point 1106C may be ignored such that it is not factored into the computations that determine the corrective motion to apply to the set of measured data points 1102 (or to the model 1104, depending on which set of points is being moved relative to the other). Excluding measured points that match to a terminal point of the model may be done to avoid pulling the model toward unsegmented branches, because those measured points would likely have matched to a more distal passageway had that more distal passageway been segmented to generate the model. In some embodiments, all measured points that match to a terminal point on the anatomic model 1104 may be ignored. The anatomic model 1104 used for registration may not represent all of the passageways of the lung or other anatomy. Accordingly, the measured points 1102 may be obtained from portions of the lung that are not included in the anatomic model 1104. The registration of the measured points 1102 to the anatomic model 1104 may be performed more efficiently and more accurately by the control system 112 by selectively ignoring a subset of measured points that does not correspond well to any of the points of the anatomic model 1104. While points that are ignored for one or more iterations may be considered in subsequent iterations in some embodiments, in other embodiments, measured points that match to more than one model point or that match to a terminal model point may be deleted from the set of measured points.

Additionally, in some situations a "terminal point" may be a most proximal point in a segment. For example, supposing segment 1104A to be the segment of the model associated with the trachea, the most proximal point would correspond to the beginning of the trachea. Points that correspond to the beginning of the trachea may be ignored for an iteration or more.

As another heuristic, timestamps associated with each measured point may be used to determine which segment the measured point is associated with. For example a timestamp associated with measured point 1102D when considered with the timestamps of other measured points recorded around the same time, may indicate that the catheter was in the passageway associated with segment 1104D and could not have been in the passageway 1104E at that time. Thus the temporal order of the measured points may be used to determine whether a given measured point may be matched to model points.

FIG. 11B shows the set of measured points 1102 and the anatomic model 1104 after a corrective motion is applied to transform the measured points 1102 for a first iteration of the registration process. For a subsequent iteration of the registration process, the measured point 1102A is now matched to a model point 1106F to which is it now closer. After the first iteration, the measured point 1102E is further away from the segment 1104A. For the first iteration, the measured point 1102C matched to the terminal model point 1106C. For the subsequent iteration, the measured point 1102C matches to a different terminal model point, point 1106G.

Figure 11D:
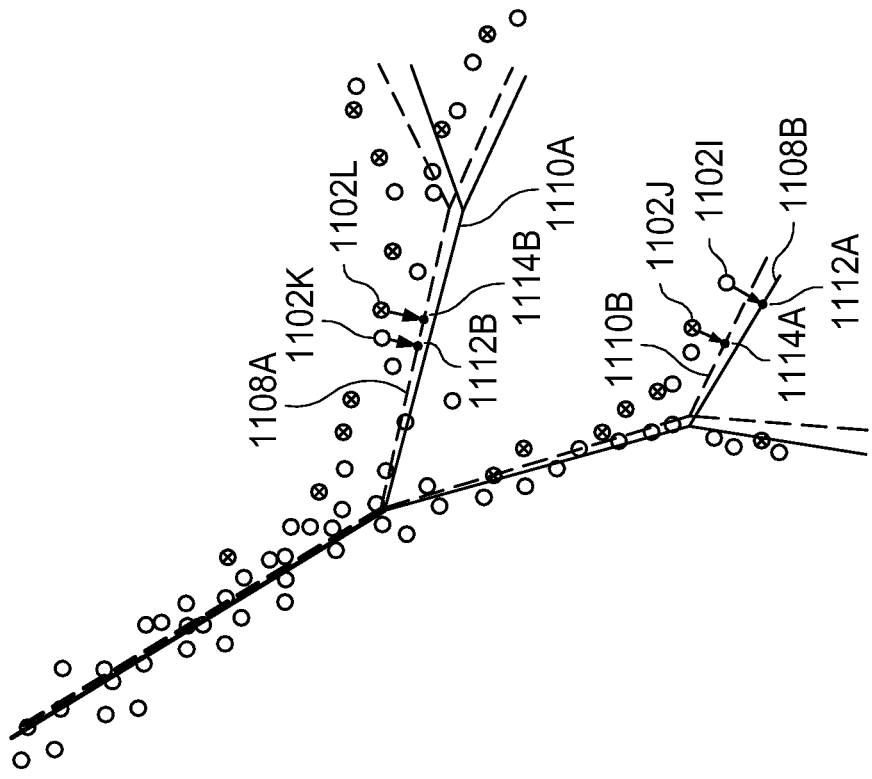
Figure 11C:
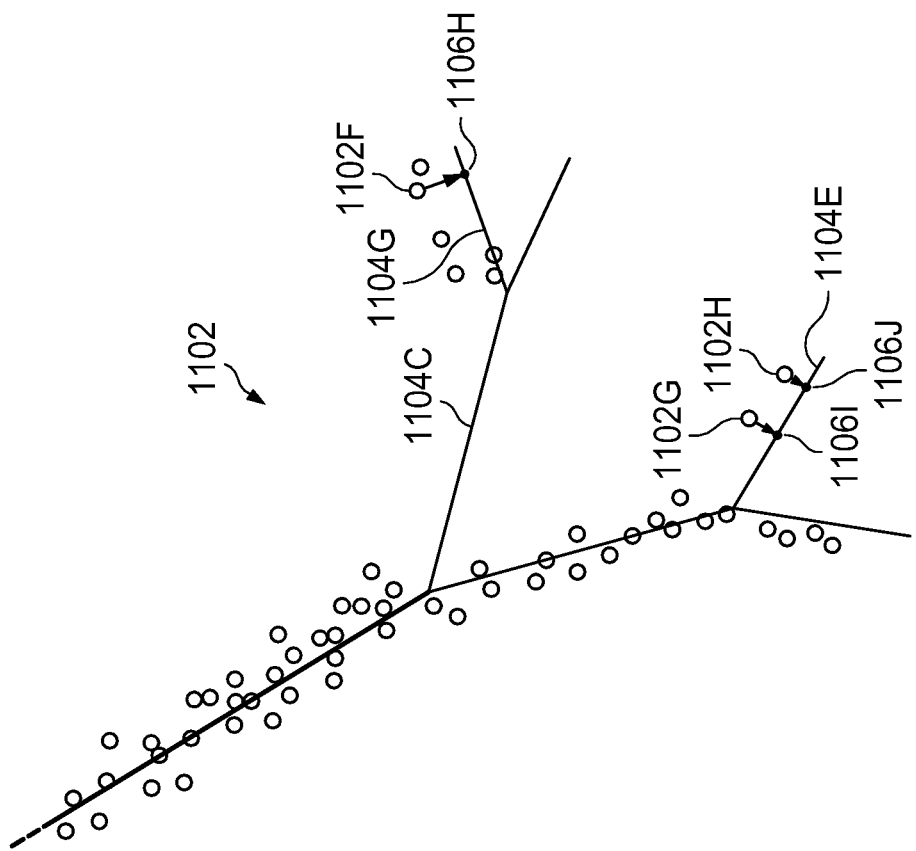

FIG. 11C illustrates another heuristic by which the process 714 of matching measured data points to model points may be optimized to provide more accurate and more efficient registration by the control system 112. As shown in FIG. 11C, a measured point 1102F is matched to a model point 1106H. Additional points of the measured points 1102 shown near the measured point 1102F will also match to points on the model segment 1104G. However, because no measured points 1102 are matched to the segment 1104C, the match between the measured point 1102F and the model point 1106H may be ignored when computing a corrective motion. This may be done on the assumption that for a point to be associated with a more distal passageway (a higher generation passageway) a measured point should be obtained that matches to the immediately prior (less distal) passageway. The immediately prior passageways may be referred to as a "parent" while the immediately distal passageway may be referred to as a "child." Here, because no measured points match to segment 1104C of the anatomic model 1104, the matches to the connecting, but more distal segment 1104G are suspect. In some embodiments, the measured point 1102F may be ignored for a specified number of iterations, e.g., one or more, or the measured point 1102F may be deleted permanently from the set of measured points 1102.

Also illustrated in FIG. 11C, two measured points 1102G and 1102H are shown matched to model points 1106I and 1106J, respectively. The model points 1106I and 1106J are part of the model segment 1104E. In some embodiments, another heuristic may provide that a threshold number of measured points is required to match to a specific model segment before the matches are considered in computing the corrective motion. For example, when a threshold of three measured points is required to match to a segment, the matches between the measured points 1102G and 1102H and the model points 1106I and 1106J, respectively, may be ignored. If, instead, the threshold value is one or two measured points, these matches may be included in the computation. In various embodiments, the threshold value may be 2, 3, 5, 10, or more points, and may depend on the generation of the passageway modeled by the segment. For example, a threshold value associated with the segment 1104G may be lower or higher than a threshold value associated with the segment 1104C because these segments are associated with different generations of passageways in the anatomic model 1104.

Referring now to FIG. 11D, shown therein are two associated anatomic models: model 1108 (the solid line model) and model 1110 (the dashed line model). The anatomic model 1108 is associated with a first respiratory phase, while the anatomic model 1110 is associated with a second respiratory phase. For example, the first respiratory phase may be an extreme of inhalation and the second respiratory phase is an extreme of exhalation while the patient P breathes. During naturally occurring processes in the body, organs, such as the lungs, may deform. In order to compensate for such processes, multiple models may be generated as shown in FIG. 11D. In FIG. 11D, the set of measured points 1102 includes points represented by data that contains a respiratory phase marker. As depicted, the points 1102 include points illustrated in FIG. 11D as circles and points illustrated therein by crosses. The points 1102 illustrated as circles include a respiratory phase marker indicating inhalation. The points 1102 illustrated as crosses include a respiratory phase marker indicating exhalation. In some embodiments, there may be separate sets of measured points stored in memory.

When the points 1102 include respiratory phase markers, another heuristic may provide that the points be matched to the corresponding phase anatomic model. As shown in FIG. 11D, while the measured point 1102I is closer to the segment 1110B, the medical system matches the measured point 1102I to a point 1112A on the segment 1108B of the anatomic model 1108. This is because the measured point 1102I includes a respiratory phase marker for inhalation and the anatomic model 1108 is a phased model associated with the inhalation phase of respiration. The measured point 1102J is matched to a model point 1114A that is part of the segment 1110B of the anatomic model 1110 because the point 1102J is an exhalation point (e.g., the data representing point 1102J includes a respiratory phase marker indicating it was obtained during exhalation) and the anatomic model 1110 is a phased model associated with the exhalation phase. Similarly, because the measured point 1102L is an exhalation point, the point 1102L matches to the model point 1114B. The point 1102K matches to the model point 1112B because they are both associated with the inhalation phase.

In embodiments where there are two phases represented in two models and the measured points each have a binary phase marker, the process 712 of FIG. 7 may be performed separately to register the first phase measured points with the first phase model and to register the second phase measured points with the second phase model. Or the separate sets of measured points may be registered with the corresponding model points. Where sets of measured points are stored separately in memory, the data representing the points may not include a phase marker. In some embodiments, the phase marker of a given measured point may be determined by measuring the phase of a patient's respiration over time and comparing this information with a timestamp associated with each measured point. When the timestamp of a given measured point indicates that the injured point was collected at the peak of inhalation, the data representing the measured point may be updated to include the appropriate phase marker. Additionally, in some embodiments in which the catheter 610 includes a shape sensor, temporal shape data may be used to determine the respiratory phase and include the appropriate markers and measured data points.

Figure 11F:
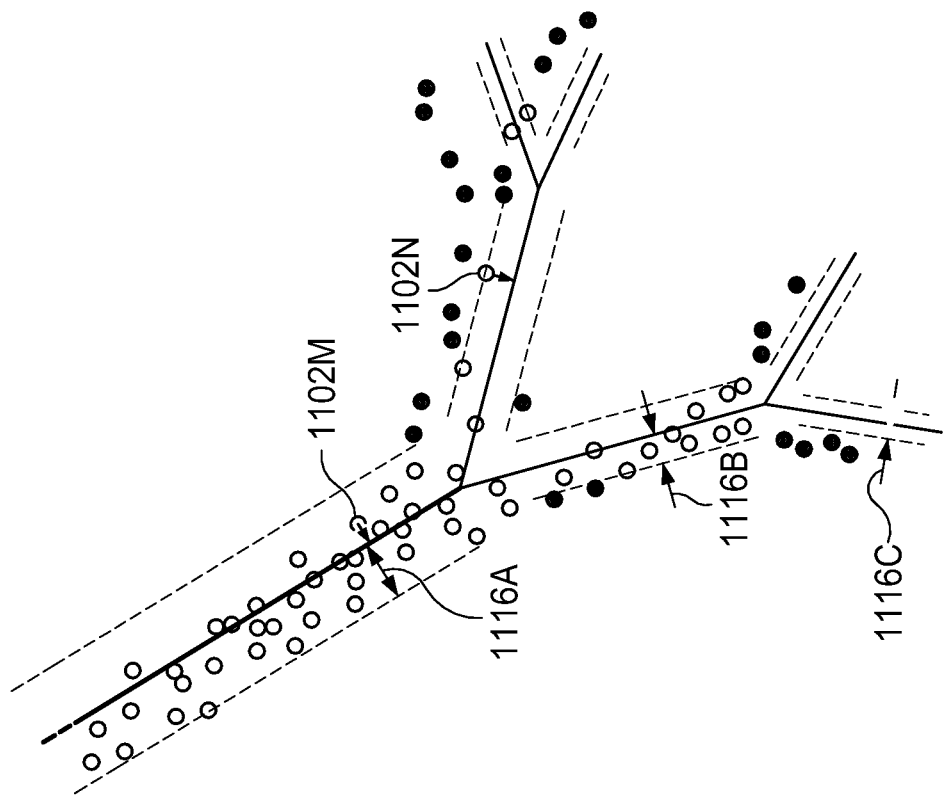
Figure 11E:
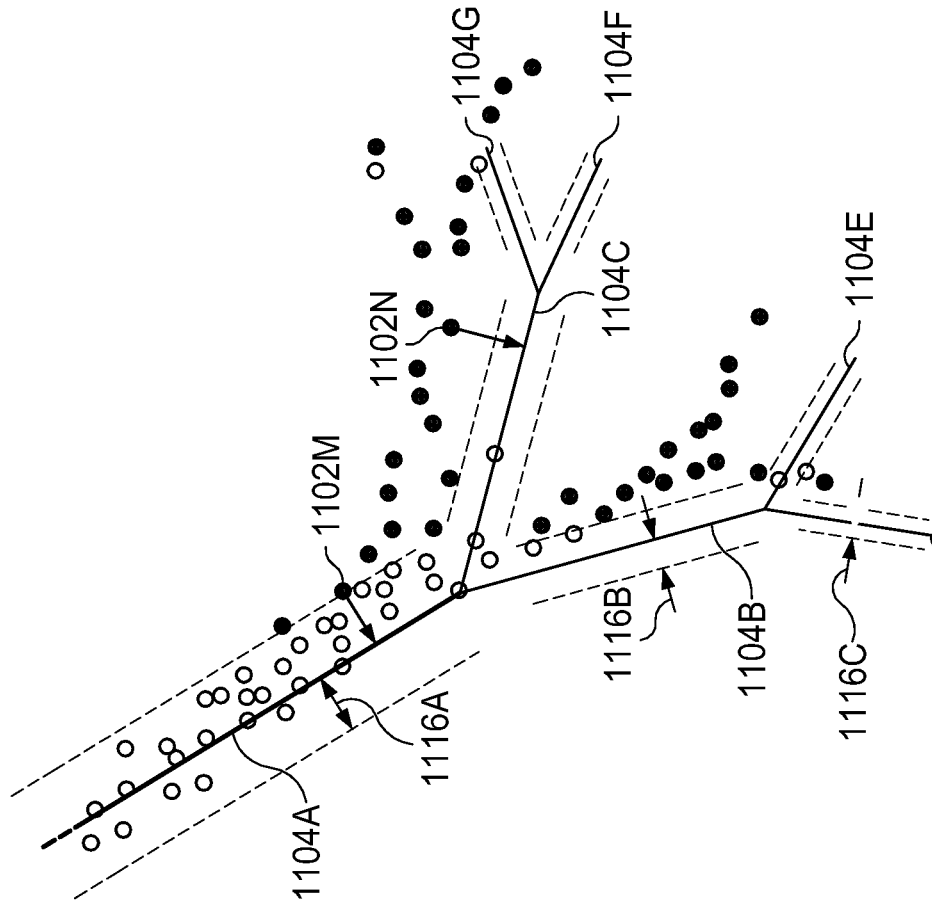

Referring now to FIGS. 11E and 11F, some embodiments of the medical system may implement a heuristic of a maximum distance threshold such that measured points that match to model points but that have a separation distance that is greater than the maximum distance threshold are excluded from the computation of the corrective motion for an iteration. As shown in FIG. 11E, the measured points 1102 have been at least initially registered with the anatomic model 1104 by a seeding process. One or more earlier iterations may have been performed as well. In some embodiments, a maximum distance threshold may be established that is applied to the anatomic model 1104 generally. Alternatively, as illustrated, a different maximum distance threshold is associated with each generation of the passageways in the anatomic model 1104. The maximum distance threshold for each generation may be determined according to characteristics such as passageway diameter and/or deformability, which affect the likelihood that a point a given distance from the centerline is a legitimate point rather than an anomaly.

As illustrated in FIG. 11E, a first maximum distance threshold 1116A is associated with the model segment 1104A, a second maximum distance threshold 1116B is associated with the model segment 1104B, and a third maximum distance threshold 1116C is associated with the model segment 1104D. Because the model segment 1104C represents a passageway of the same generation as the passageway represented by the model segment 1104B, the second maximum distance threshold 1116B may also be associated with the segment 1104C. Similarly, the segments 1104E, 1104F, and 1104G, are all associated with the same generation of passageway as the segment 1104D. Accordingly, the third maximum distance threshold 1116C may also be associated with the segments 1104D, 1104F, and 1104G. These maximum distance thresholds 1116A, 1116B, and 1116C may correspond with an average passageway radius obtained from a plurality of patients or they may be obtained from a model of the specific patient P.

In some embodiments, the maximum distance thresholds 1116A, 1116B, and 1116C may be related to an average passageway radius obtained from the patient P specifically. For example, the maximum distance thresholds may be obtained based on passageway radius calculations from the segmented model 502 illustrated in FIG. 5A. Because the more distal passageways may have smaller radii than the more proximal passageways, the maximum distance thresholds for the more distal passageways may generally be less than the maximum distance thresholds for the more proximal passageways.) In some embodiments, the maximum distance threshold may be greater than approximately the diameter of the passageway (i.e., greater than approximately twice the radius). In some embodiments the maximum distance threshold may be approximately one and a half times the radius of the passageway. In some embodiments, the maximum distance threshold may be about 20 mm for the trachea and as small as around 2 mm for distal passageways. In some embodiments, the maximum distance threshold may decrease from the trachea for one or two generations and then increase again to account for the increased likelihood of deformation in the more distal passageways.

As illustrated in FIG. 11E, the measured point 1102M is matched to a point on the segment 1104A. However, the separation distance between the measured point 1102M and the segment 1104A is greater than the maximum distance threshold 1116A and so the match may be ignored when computing the corrective motion to be applied to the set of measured points 1102. Similarly, the measured point 1102N is further away from the segment 1104C than the maximum distance threshold 1116B and so may also be ignored.

Referring now to FIG. 11F, shown therein is the result of the corrective motion computed based on the set of measured points 1102 and the anatomic model 1104 as illustrated in FIG. 11E. Due to the corrective motion, the measured points 1102M and 1102N are position within maximum distance threshold 1116A and 1116B, respectively. Accordingly, the matches between the measured points 1102M and 1102N and the closest points in segments 1104A and 1104C, respectively, may be included by the maximum distance heuristic as factors in the computation of the corrective motion of the subsequent iteration.

The maximum distance thresholds may be applied in other ways. For example, the maximum distance threshold may be provided as a function of generation, or as a function of distance from a specific feature, such as the main carina. The maximum distance threshold may also be calculated as a function of depth into the passageways. Accordingly, the maximum distance threshold may be larger at a proximal end of a model segment, such as the model segment 1116B, then at a distal end of that model segment.

Figure 11H:
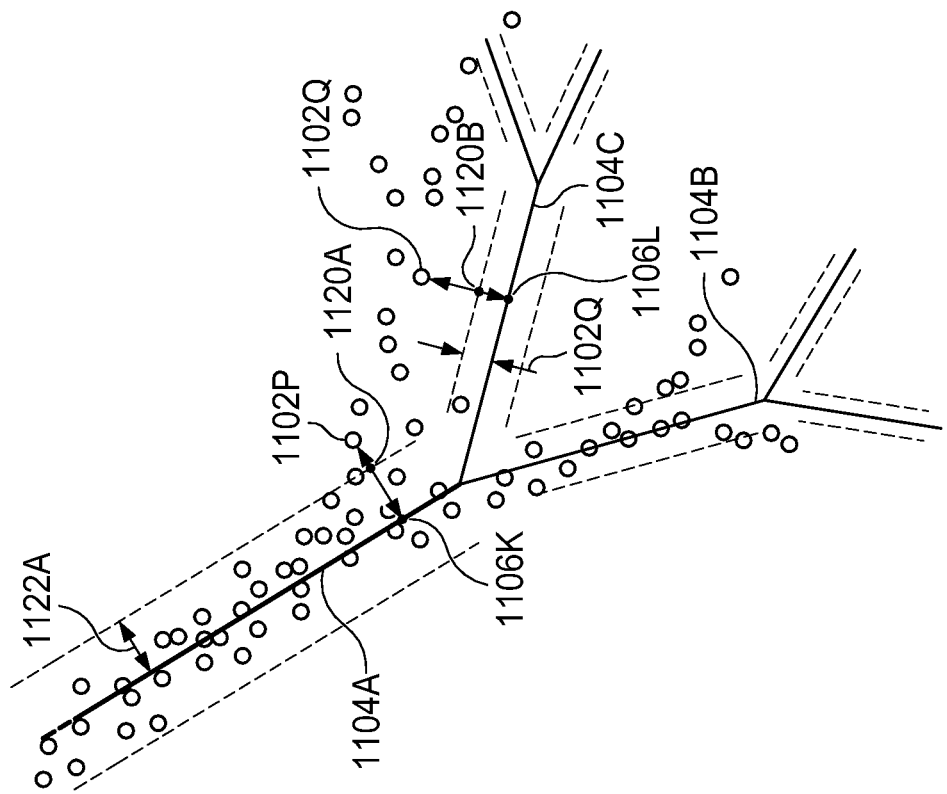
Figure 11G:
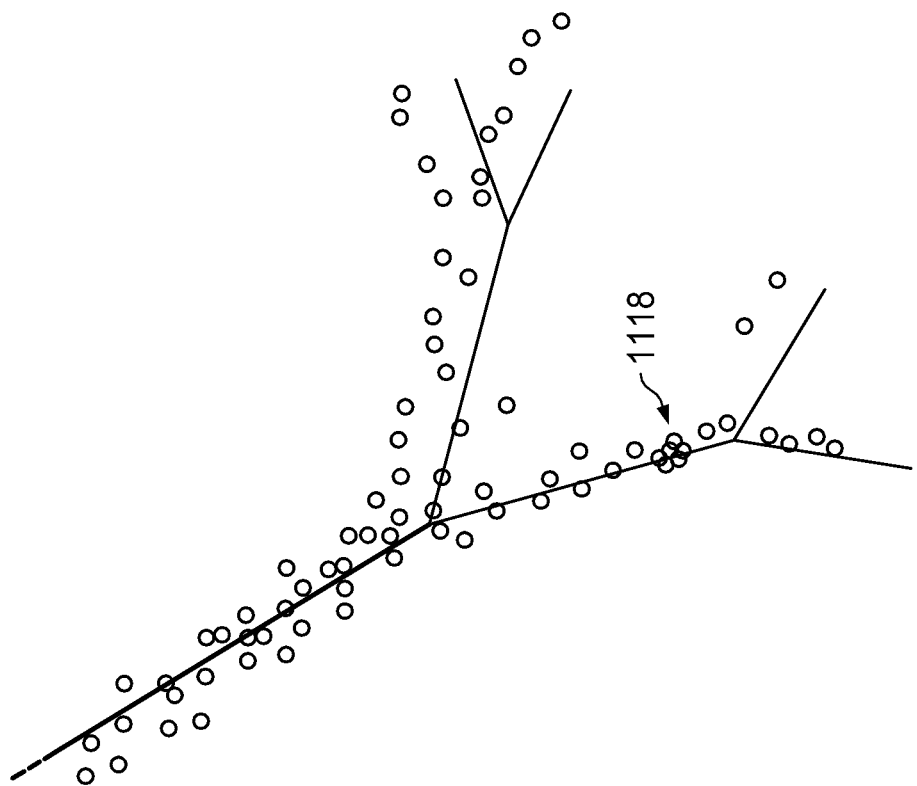

Referring now to FIG. 11G, in some embodiments if the point gathering instrument is not moved for a period of time, multiple points may be measured in a single location or very close together. As shown in FIG. 11G, there is a cluster 1118 of measured points 1102. Because the cluster includes so many points, the collection of measured points at the location of the cluster 1118 may skew the results of the computation to determine the corrective motion by including multiple matches. In order to filter out this result, the distance between the measured points 1102 may be compared to identify clusters. Alternatively or additionally, clusters, like the cluster 1118, may be identified by determining the distance between measured points that are in sequence by timestamp. This may allow for the identification of a cluster caused by a pause in movement of the catheter 610 rather than by a narrowing of a passageway. As another heuristic, the measured points in the cluster 1118 and/or associated matches may be ignored. In some embodiments, the cluster 1118 may be permanently deleted in order to avoid having to screen out the cluster 1118 in subsequent iterations of the registration process 712.

Referring now to FIG. 11H, shown therein in another heuristic that may be used in matching measured points 1102 to the anatomic model 1104. FIG. 11H includes a plurality of artificial model points 1120 that are generated based on the anatomic model 1104. The artificial model points 1120 may be incorporated into the anatomic model 1104 for one or more iterations before being discarded in subsequent iterations. New artificial model points may be calculated for each iteration, in some embodiments. When the matching process is performed one or more artificial points 1120 may be generated based on the measured points and the radius of the matched passageway. For example, the artificial point 1120A may be generated based on the measured point 1102P. As shown in FIG. 11H, the measured point 1102P is further away from its closest point on model segment 1104A (point 1106$k$) than the radius 1122A. The artificial point 1120A is created along the line between the model point 1106$k$ and the measured point 1102P at a distance no greater than radius 112A from the model point 1106$k$. The artificial point 1102A may then be added to the set of model points for the next iteration. For that iteration the measured point 1102P is matched to the artificial point 1120A and the resulting match is used to compute the corrective motion to be applied to the set of measured points 1102.

As shown in FIG. 11H, another artificial model point 1120B is generated along the line connecting the measured point 1102Q to the nearest model point 1106L. The artificial point 1120B is defined along that line at a distance, equal to radius 112B, from the model segment 1104C. As shown in FIG. 11H, the segments 1104A, 1104B, and 1104C include artificial points of the artificial model points 1120. The artificial model points 1120 that border the segment 1104A are positioned up to a radial distance 1122A away from the segment 1104A. While illustrated in two dimensions in FIG. 11H, the artificial model points 1120 may simulate a two-dimensional plane or a volume. For example, the artificial point 1120A may be closer to the model point 1106$k$ than the radius 1122A when the measured point 1102P is closer than the radius 1122A to the model point 1106$k$. In such cases, the artificial point 1120A may be at the same location as the measured point 1102P itself. Other heuristics may then be applied to determine whether the matches between the measured point 1102P and the artificial point 1120A and between the measured point 1102Q and the artificial point 1120B are included in the computation of the corrective motion. For example, if the distance between the artificial point 1120B and the measured point 1102Q is greater than a maximum threshold distance, the match may be discarded for that iteration.

In some embodiments, the heuristics above and other heuristics may be used in combination to prevent one or more measured points from being matched or to prevent one or more matches from being factored into the computation of the corrective motion. Thus, heuristics may be employed by the control system 112 in series (e.g., one heuristic per iteration) or in parallel (e.g., multiple heuristics operating in a single iteration).

In some embodiments, other heuristics may be used to assigned weights to measured points. Additionally in some embodiments, the control system 112 may guide a clinician in obtaining measured points to use in registering and anatomic model. For example, certain passageways in the upper lobe of each lung may provide particularly reliable and useful information for registering and anatomic model to a patient undergoing a procedure. Accordingly, in some embodiments a user interface may be displayed by the control system 112 in the display system 110 to a clinician. The user interface may direct the clinician to steer a catheter into high information locations within the upper lobes of the lungs. In some embodiments, one or more measured points may be ignored such that the measured points are not matched in a matching process to model points. In some embodiments, one or more matches may be ignored such that the matches are not included in the computation of the corrective motions. Thus, heuristics may be applied to points as well as to matches.

Referring again to FIG. 7, at process 724 the localized instrument may be displayed with the anatomic model to assist the clinician in an image-guided surgery. FIG. 12 illustrates a display system 1200 displaying, in a user interface, a rendering of anatomic passageways 1202 of a human lung 1204 based upon anatomic model information. With the patient surgical space registered to the model space as described above in FIG. 10, the current shape of the catheter 610 and the location of the distal end 618 may be located and displayed concurrently with the rendering of the passageways 1202. The anatomic model information may be obtained from measured data points, moved data points, registered data points, and other data points described herein may be displayed on the display 110 in a visual representation. The data points may be visually represented in a user interface by a plurality of points or dots on the display or as a rendered model, such as a mesh or wire model created based on the set of data points. In some embodiments, a visual representation may be refreshed in the display 110 after each processing operations has been implemented to alter the data points.

As shown in FIG. 13, in some embodiment, the control system 112 may adjust weights associated with one or more of the points to alter their effects as factors in the computation of the corrective motions. The weights may be adjusted based on one or more factors. Shown in FIG. 13 is a set of measured points as stored in a point pool 1300 in memory of the control system 112. The exemplary point pool 1300 contains data representing the measured points obtained from within the patient P. In the point pool 1300, each point includes a point identifier, a set of coordinates, a timestamp, a sensor ID, a phase marker, and a weight. Some embodiments may include the timestamp as the point identifier instead of a separate point identifier. This data may be formatted in many different ways. As shown in FIG. 13, the phase marker is a binary value, either 0 or 1, depending on whether the phase is inhalation or exhalation, respectively. Other phase markers may be used in other embodiments. The weights as shown in the exemplary point pool 1300 are normalized weights. Some embodiments, such as those using a shape-sensing catheter may not include a sensor ID, which may be used by catheters having a plurality of EM sensors or a plurality of other discrete sensors that can be identified to determine approximately where on the catheter the data point was measured.

In some embodiments of the method 700 of FIG. 7, the registration process 712 may include an additional process in which weights for measured points are altered according to parameters or rules. The weights may be altered by adding a weight where no weight existed before or by changing the weigh associated with a given measured point. For example, in some embodiments more recently obtained points may be assigned a relatively higher weight. The relatively higher weight may be provided by incrementally decreasing the weights assigned to less recently obtained points as more time passes. More recently measured points may be more accurate due to movement of the patient, so by weighting the more recently measured points more than the less recently measured points the registration process 712 may be biased to reflect the most current information. The weights may be normalized weights or non-normalized.

In some embodiments, the weight of a given measured point may be based on the generation of the passageway in which the point was obtained. For example, as shown in FIG. 11A, the anatomic model 1104 includes several segments 1104A, 1104B, and 1104C and others that are associated with specific generations of passageways. Because the trachea is a broader passageway, and so provides less information with which to register the measured points to the modeled points, measured points that match to the segment 1104A be having a relatively reduced weight. Similarly, measured points that match to the segment 1104C and other of the same more distal generation may be assigned a relatively reduced weight as well. The measured points associated with the more distal generations may be assigned less weight because these more distal passageways are more likely to deform due to the forces exerted by the point gather instrument on the passageways. The segment 1104B is associated with a more central passageway that is narrower than the segment 1104A and more resilient to deformation by the catheter 610 than the segment 1104C.

In order to compensate for the deformation that can be caused by the point gathering instrument used to obtain the points in the point pool 1300, the weight of each point may be based on the state of the catheter. For example, the catheter may include a torque sensor, and when high torque is indicated a lower weight may be assigned as the high torque may indicate significant deformation. Similarly, if the catheter is in a controlled state such that the distal end of the catheter is actively positioned in a central portion of the passageway through which is the catheter is passing the measured point may have a relatively higher weight than if the catheter is in a flaccid state. In some embodiments, the measured points may be collected into the point pool 1300 only when the catheter is actively being steered and controlled in order to collect points from the center of the passageways. When in the flaccid state the catheter may be more likely to pass along the bottom of the passageway than when in the active, controlled state. In some embodiments, the measured points collected in the flaccid or passive state may be compensated with an adjustment to make it as if the points were collected closer to the center of the passageway. This may be done by altering the coordinates of the collected points to move the point toward the center. Additionally, in order to minimize deformation caused by inserting a catheter further into passageways, some embodiments may limit point collection to when the catheter is in a passive state and is being retracted from the passageways. When a camera is provided on the distal end of the catheter, using image-recognition techniques the control system may determine based on obtained images, whether the catheter is in the middle of the passageway. The control system may limit point collection to when the catheter is in the middle as indicated by image-recognition.

Weights may be assigned based on the respiratory phase in which a measured point is collected. Thus, when a single anatomic model is used the measured points that are similar in phase to the single anatomic model (like the anatomic model 1108 of FIG. 11D) may be given greater weight than the measured points that are associated with a different phase.

When measured points can be collected by the catheter at multiple locations along its length, whether due to the inclusion of a shape-sensor or a plurality of discrete sensing/transmitting devices, the history of the catheter may be used to assign weights. As the catheter is advanced through the passageways of the patient's anatomy, multiple points are collected along its length. A less distal portion of the catheter may collect a point that has the same or substantially similar coordinates as a point collected earlier by a more distal portion of the catheter. Alternatively, if the catheter is being withdrawn from a vessel rather than being advanced, the coordinates of a point obtained by the distal end of the catheter may be the same or substantially similar to the coordinates of a point obtained earlier by a less distal portion of the catheter. In some embodiments, the measured points are only collected using the catheter when the catheter is being withdrawn from the passageways of the patient. This history may indicate that the recurring point is particularly reliable and the weights of either or both of the earlier obtained point and the later obtained point may be adjusted to be relatively higher. In some embodiments, the points measured by more distal portions of the catheter may be weighted higher than less distal portions of the catheter, because the less distal portions of the catheter may be thicker in diameter and more likely to cause deformation of tissue. Other configurations of the catheter may also be used as factors upon which to base weights for measured points.

In some embodiments, machine learning may be used to identify qualities of the most reliable points. The control system may then apply weights accordingly. Each of the described factors may be used to determine the weight of a single point. Thus, while a single factor may be used to determine the weight of a given point in some embodiments, in other embodiments multiple factors may be used by the control system to adjust the weight of one or more of the points in the point pool 1300.

Referring again to FIGS. 6A and 6B, shown therein is a tracking device 624 temporarily affixed to the patient P. By monitoring the tracking device 624 the control system may determine whether the patient P moves. The tracking device 624 may be a device capable of generating position and or movement data, such as a set of EM sensors/transmitters, accelerometers, etc. In some embodiments the tracking device 624 may be a passive device that is monitored by a monitoring device. For example, the tracking device 624 may be a pad that is easy to identify by a visual tracking system. For example, the pad may have known dimensions and may include a distinctive pattern and/or color to allow machine vision to monitor its location. When the tracking device 624 moves, the visual tracking system may provide an indication to the control system that the patient P has moved.

Due to movement of the patient P, a previous registration between an anatomic model and measured points may become less accurate. Accordingly information obtained from and/or displayed in connection with the anatomic model, such as a lesion or tumor, may not be accurately communication to a clinician. In some embodiments, after a satisfactory registration has been obtained and movement of the patient P is detected, the registration process may begin again. In some embodiments, a change in displacement and/or orientation measured by the tracking device 624 may be used to update the registration. In some embodiments, the registration process 712 may be performed again beginning with a seeding process. In other embodiments, the registration process 712 may be performed without performing a new seeding process. For example, if the movement of the patient P is determined to be small, discarding older measured points from the point pool 1300 (or decreasing their relative weighting substantially in favor of points obtained after the detection of the movement of patient P) and collecting new measured points using the catheter. Thus in some embodiments, a new set of points is collected and used to register the model to the moved patient P or a mixed weighting of new and old points may be used. In some embodiments, a notification is provided to a user to initiate a registration due to patient movement. In other embodiments, registration may be initiated by the control system 112 after motion in the tracking device 624 is detected.

In some embodiments, the shape of the catheter after the movement of the patient P may be used to compensate for errors in the rigid registration due to the motion. In some embodiments, the shape sensor data may be used to provide new measured points after the movement of the patient P that may be used to perform further registration processes, like those in the method 700.

In some embodiments, the point gathering instrument is coupled to a teleoperational robotic arm. The teleoperational arm may move according to commands from an operator input system. In some embodiments, the insertion stage 608 may be mounted on a teleoperational arm. When the arm or the insertion stage 608 moves, the movement may be communicated to a control system from encoders incorporated into the setup joints of the arm and/or the stage 608. When the insertion stage 608 and/or the teleoperational arm move as indicated by the encoders, the registration process may be performed again. A comparison between the commanded motion and the measured motion (with the shape sensor) may indicate that movement has occurred that was not commanded. If the comparison value between the commanded motion and the measured motion exceeds a threshold value, all or a portion of the registration process may be reinitiated. This may occur, for example, if the distal tip was commanded to enter the opening of a passageway but is dislodged from the entrance to the opening due to anatomical motion, tissue texture, or other anatomic forces.

Referring now to FIG. 14, a flowchart of a method 700A is shown therein. The method 700A shares many of the processes included in the method 700 as described herein and as illustrated in FIG. 7. The shared processes include the same reference numerals. The method 700A further includes a set of processes that provide a method for initiating the collection of measured points within the patient passageway. The method 700A may be implemented as part of a workflow managed by the control system 112 to enable clinicians to more effectively and efficiently treat patients like the patient P.

The collection of location and/or shape data to generate a set of measured points describing the passageways of the patient P's anatomy may begin automatically when the point gathering instrument (e.g., the catheter 610) is introduced into the patient passageways. This may be performed at process 1402 in which the control system 112 detects one or more point collection conditions that trigger the collection of measured points. For example, when the catheter 610 includes a camera or image sensor, images may be collected and processed to determine when the distal end 618 enters the patient passageways. For example, the control system 112 or another component of the system 100 may identify the appearance of the main carina obtained by the image sensor system or may identify the trachea from the colors of images obtained therein.

Also, as described herein in connection with FIGS. 6C and 6D, the ET tube 622 may include colors and or patterns on the interior surface 623 thereof. When images obtained from the catheter 610 during introduction into the patient passageways do not include the colors and/or patterns of the interior surface 623, this may provide a point collection condition. When information obtained from the images indicates that the transition from the interior of the ET tube 622 to the interior to the trachea (or other anatomic passageway) is completed, the point collection condition may be detected.

Additionally, as described in connection with FIGS. 6A and 6B, the position measuring device 620 provides information about the position of the rigid instrument body 612 as it moves on the insertion stage 608 along an insertion axis A. The movement of the rigid instrument body 612 may provide an indication of the movement of the distal end 618 of the catheter 610. This kinematic information may be used to infer that, after a certain amount of insertion motion, the catheter 610 is likely to have entered patient passageways. Thus, the kinematic information may provide a collection condition that, when detected, can trigger the process 1404 of initiating the collection of location information to collect a set of measured points describing the patient passageways. Similarly, where the catheter 610 is coupled to another robotic device such as a robotic arm, the kinematic information provided by encoders in the arm of device may be used to detect a point collection condition, such as an amount of movement in a specific direction. In some embodiments, the movement commands provided to the robotic device or arm may also be used to identify a point collection condition that triggers the collection of points at process 1404, rather than relying on encoders to relay the actual movements. In some embodiments, both the commanded motion and the measured motion of the robotic device may be used. When sufficient motion is detected and/or commanded, the control system 122 may detect the motion and determine whether it satisfies requirements of a point collection condition.

Although the systems and methods of this disclosure have been described for use in the connected bronchial passageways of the lung, they are also suited for navigation and treatment of other tissues, via natural or surgically created connected passageways, in any of a variety of anatomic systems including the colon, the intestines, the kidneys, the brain, the heart, the circulatory system, or the like.

At the process 1404, the data representing the points may be added to the point pool 1300, stored in memory, as shown in FIG. 13. This location information represented by the measured points may be collected exclusively at the distal end 618 of the catheter 610, from a plurality of discrete points along the length of the catheter, or obtained from shape-sensor information continuously along the length of the catheter 610. When the shape-sensor information provides position information continuously along the length of the catheter 610, the shape-sensor information may be sampled to generate discrete points, in some embodiments. Depending on how the points are obtained from the catheter (and the type of catheter used for point collection) the detection of a point collection condition for collection of points from a certain portion of the catheter may not be sufficient to trigger the collection of points at another portion of the catheter. For example, when the distal end 618 transitions from the ET tube 622 to the trachea, the condition may be satisfied so as to trigger collection of points at the distal end 618, but not at a portion of the catheter that is still in the ET tube 622. Thus, in some embodiments, after the distal end 618 exits the tube as recognized by the visual information provided to the control system 112, kinematic information may be used to determine when to begin point collection from less distal portions of the catheter. When the catheter 610 includes a plurality of EM sensors distributed along its length, the distance of insertion may be used to determine when to begin collecting information. For example, if the second EM sensor is positioned 2 cm from a first EM sensor at the distal end of the catheter, the point collection condition for the second EM sensor may be that the first EM sensor must have exited the ET tube 622 and the catheter must have been moved 2 cm or another predetermined distance. The movement is obtained from kinematic information as described herein.

In some embodiments, the registration process, like that described in process 712 of FIG. 7, may be repeated during the course of a surgical procedure. As described, a movement of the patient P may trigger a new registration process. In some embodiments, the registration algorithm is executed by the control system 112 periodically, such as every minute or every five minutes during the procedure. In other embodiments, the registration process may be constantly run on the control system 112 as a background process and continuously updated. For example, even after a registration process is complete, the collection of measured points in the point pool 1300 may continue as long as a catheter capable of obtaining the measured points (from any suitable modality) is present within the patient passageways. In some embodiments in which the registration process operates as a background process, the registration may only be updated when a new registration is superior to an old registration as determined by an accuracy metric. The accuracy metric may be the percentage of measured points successfully matched to the model or may be the average distance between the measured points and the matched model points. Other accuracy metrics may be implemented in other embodiments. Thus, when a more recent registration has a greater percentage of measured points successfully matched, the more recent registration may be used instead of an older registration. By requiring that an accuracy metric be met in order to replace one registration with another, consistency is maintained unless a superior registration is obtained.

In some embodiments, when a later registration replaces an earlier registration or an earlier registration is deemed replaceable by the control system 112 with a later registration, an alert may be provided to the clinician through a user interface to indicate that there is a change in registration or that there is a superior registration available. In some embodiments, the control system 112 may require clinician approval through the user interface before the superior registration is implemented. For example, when a superior registration is identified an alert may be rendered to the display system 110 along with a button or other user interface element by which the clinician can approve or disapprove to the new registration. The new registration will then be implemented or not depending on the clinician's decision.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processor thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
   segmenting a set of first modality image data representing a model of one or more passageways within a patient;
   generating a first set of points based on the segmented set of first modality image data representing the model of the one or more passageways;
   registering the first set of points to a second set of points by:
   determining a set of matches between the second set of points and the first set of points, wherein the second set of points is obtained by a second modality; and
   discarding a first subset of the set of matches based on a first heuristic to generate a modified set of matches, wherein discarding the first subset of the set of matches comprises ignoring an associated set of matches between the first set of points and the second set of points when computing a corrective motion to be applied to the second set of points, and wherein at least one ignored match is included in a second subset of the set of matches when computing a second corrective motion to be applied to the second set of points; and
   displaying a visual representation of the one or more passageways based on the modified set of matches in a user interface provided by a display.

2. The method of claim 1, wherein the second set of points is a set of measured points obtained from the patient during a medical procedure.

3. The method of claim 1, further comprising moving the second set of points relative to the first set of points based on the set of matches, wherein moving the second set of points relative to the first set of points comprises applying the corrective motion to the second set of points.

4. The method of claim 1, wherein the second modality is electromagnetic sensing and the second set of points are obtained using a catheter comprising one or more electromagnetic sensors disposed thereon.

5. The method of claim 1, wherein the second modality is fiber optic shape-sensing and the second set of points are obtained using a catheter comprising a shape sensor extending therein.

6. The method of claim 5, wherein the shape sensor provides data that is sampled to obtain discrete points for the second set of points.

7. The method of claim 1, wherein the first modality is one of computed tomography (CT), magnetic resonance imaging (MRI), fluoroscopy, thermography, ultrasound, optical coherence tomography (OCT), thermal imaging, impedance imaging, laser imaging, or nanotube X-ray imaging.

8. The method of claim 1, wherein generating a first set of points based on the segmented set of first modality image data comprises:
  generating a line corresponding to a center of each of the one or more passageways; and
  generating a plurality of centerline points to provide the first set of points.

9. The method of claim 1, wherein the model of the one or more passageways comprises an indication of a generation of each of the one or more passageways.

10. The method of claim 1, wherein a catheter used to obtain the second set of points is teleoperationally controlled.

11. The method of claim 1, further comprising:
  moving the second set of points relative to the first set of points based on the set of matches;
  determining a second set of matches between the moved second set of points and the first set of points;
  discarding a subset of the second set of matches based on the first heuristic to generate a newly modified set of matches; and
  moving the moved second set of points relative to the first set of points based on the newly modified set of matches.

12. The method of claim 1, further comprising:
  moving the second set of points relative to the first set of points based on the set of matches;
  determining a second set of matches between the moved second set of points and the first set of points;
  discarding a subset of the second set of matches based on a second heuristic to generate a newly modified set of matches; and
  moving the moved second set of points relative to the first set of points based on the newly modified set of matches.

13. The method of claim 1, further comprising discarding a subset of the second set of points based on a second heuristic.

14. The method of claim 1, wherein the first heuristic comprises at least one of a terminal model point heuristic, a multiple match heuristic, a maximum distance heuristic, a time-based heuristic, or a phase-based heuristic.

15. A method comprising:
  segmenting a set of first modality image data representing a model of one or more passageways within a patient;
  generating a first set of points based on the segmented set of first modality image data representing the model of the one or more passageways;
  accessing a second set of points collected from within the patient, wherein the second set of points is obtained by a second modality; and
  registering the first set of points to the second set of points by:
    discarding a first subset of the second set of points based on a first heuristic to generate a modified second set of points, wherein discarding the first subset of the second set of points comprises ignoring an associated set of matched points of the second set of points when computing a corrective motion to be applied to the second set of points, and wherein at least one ignored point is included in a second subset of the second set of points when computing a second corrective motion to be applied to the second set of points;
    determining a set of matches between the modified second set of points and the first set of points; and
    moving the second set of points relative to the first set of points based on the set of matches.

16. A system comprising:
a processor; and
a memory having computer readable instructions stored thereon, the computer readable instructions, when executed by the processor, cause the system to:
  segment a set of first modality image data representing a model of one or more passageways within a patient;
  generate a first set of points based on the segmented set of first modality image data representing the model of the one or more passageways;
  register the first set of points to a second set of points by:
    determining a set of matches between the second set of points and the first set of points, wherein the second set of points is obtained by a second modality; and
    discarding a first subset of the set of matches based on a first heuristic to generate a modified set of matches, wherein discarding the first subset of the set of matches comprises ignoring an associated set of matches between the first set of points and the second set of points when computing a corrective motion to be applied to the second set of points, and wherein at least one ignored match is included in a second subset of the set of matches when computing a second corrective motion to be applied to the second set of points; and
  display a visual representation of the one or more passageways based on the modified set of matches in a user interface provided by a display.

17. The system of claim 16, wherein the second set of points is a set of measured points obtained from the patient during a medical procedure.

18. The system of claim 16, wherein the computer readable instructions, when executed by the processor, further cause the system to move the second set of points relative to the first set of points based on the set of matches, wherein moving the second set of points relative to the first set of points comprises applying the corrective motion to the second set of points.

19. The system of claim 16, wherein the first modality is one of computed tomography (CT), magnetic resonance imaging (MRI), fluoroscopy, thermography, ultrasound, optical coherence tomography (OCT), thermal imaging, impedance imaging, laser imaging, or nanotube X-ray imaging.

20. The system of claim 16, wherein the second modality is fiber optic shape-sensing and the second set of points are obtained using a catheter comprising a shape sensor extending therein.

* * * * *